United States Patent [19]

Rubinstein et al.

[11] Patent Number: 5,723,438
[45] Date of Patent: Mar. 3, 1998

[54] METHOD OF ANTIVIRAL USE OF SOLUBLE LDL RECEPTOR

[75] Inventors: Menachem Rubinstein, Givat Shmuel; Daniela Novick, Rehovot; Nathan Tal, Rehovot; Dina G. Fischer, Rehovot, all of Israel

[73] Assignee: Yeda Research and Development Co. Ltd., Rehovot, Israel

[21] Appl. No.: 485,131

[22] Filed: Jun. 7, 1995

Related U.S. Application Data

[60] Division of Ser. No. 92,817, Jul. 19, 1993, Pat. No. 5,496,926, which is a continuation-in-part of Ser. No. 4,863, Jan. 19, 1993, abandoned.

[30] Foreign Application Priority Data

| Jan. 19, 1992 | [IL] | Israel | 100696 |
| Aug. 23, 1992 | [IL] | Israel | 102915 |

[51] Int. Cl.$^6$ .......... A61K 38/17; A07K 14/705
[52] U.S. Cl. .......... 514/2; 530/350; 424/545
[58] Field of Search .......... 514/2; 530/350; 424/545

[56] References Cited

U.S. PATENT DOCUMENTS

| 4,454,115 | 6/1984 | Borden et al. | 424/85.6 |
| 4,614,651 | 9/1986 | Jarvis et al. | 424/85.4 |
| 4,745,060 | 5/1988 | Brown et al. | 435/172.3 |
| 5,208,144 | 5/1993 | Smith et al. | 435/6 |

FOREIGN PATENT DOCUMENTS

| 0586094 | 7/1993 | European Pat. Off. . |
| 9401553 | 1/1994 | WIPO . |

OTHER PUBLICATIONS

Schneider et al., "Purification of the Low Density Lipoprotein Receptor, An Acidic Glycoprotein of 164,000 Molecular Weight", *J. Biologial Chemistry* 257:2664–2773 (1982).

Weil et al., *Nature*, vol. 301, p. 437, 1983.

Thomas et al., *Methods in Enzymology*, vol. 182, p. 499, 1990.

Spear, G. Journal of Virology Dec. 1990, vol. 64, No. 12 pp. 5869–5873.

*Primary Examiner*—Stephen Walsh
*Assistant Examiner*—Daryl A. Basham
*Attorney, Agent, or Firm*—Browdy and Neimark

[57] ABSTRACT

A soluble LDL receptor protein is provided. It can be isolated from cells that have been treated with an interferon, isolated from the urine of healthy human individuals or produced by recombinant techniques. The soluble LDL receptor protein is useful in protection of meals against viral infections.

5 Claims, 19 Drawing Sheets

FIG. 10

| AAcid # | AAcid ID | R.Time (min) | C.Time (min) | Pmol (raw) | Pmol (-bkgd) | Pmol (+lag) | Pmol Ratio | AAcid ID |
|---|---|---|---|---|---|---|---|---|
| 1 | D | 5.43 | 5.58 | 16.70 | 12.03 | 13.23 | 53.94 | ASP |
| 2 | R | 15.62 | 15.62 | 6.52 | 3.83 | 4.25 | 12.16 | ARG |
| 3 | P | 19.73 | 19.68 | 6.66 | 1.58 | 2.11 | 4.26 | PRO |
| 4 | E | 9.35 | 9.50 | 12.53 | 5.10 | 6.74 | 14.78 | GLU |
| 5 | R | 15.67 | 15.62 | 4.91 | 2.40 | 3.13 | 8.95 | ARG |
| 6 | N | 6.17 | 6.27 | 8.89 | 6.71 | 8.33 | 17.43 | ASN |
| 7 | E | 9.35 | 9.50 | 11.22 | 4.47 | 5.78 | 12.67 | GLU |
| 8 | F | 25.07 | 25.00 | 7.34 | 5.57 | 7.38 | 32.77 | PHE |
| 9 | Q | 7.53 | 7.68 | 8.35 | 5.04 | 6.68 | 38.64 | GLN |
| 10 | | | | | | | | |
| 11 | Q | 7.52 | 7.68 | 5.18 | 1.93 | 2.37 | 13.01 | GLN |
| 12 | D | 5.43 | 5.58 | 7.10 | 3.42 | 5.31 | 21.65 | ASP |
| 13 | G | 8.65 | 8.80 | 14.84 | 2.66 | 3.43 | 3.31 | GLY |
| 14 | K | 26.20 | 26.13 | 2.63 | 0.79 | 0.79 | 2.14 | LYS |
| 15 | P | 19.70 | 19.68 | 5.03 | 1.46 | | 2.36 | PRO |

REPETITIVE YIELD ANALYSIS:

| | | | Rep.Yield | Variance |
|---|---|---|---|---|
| D: | 1,12 | :ASP | 89.21 % | 1.000 |
| R: | 2, 5 | :ARG | 85.52 % | 1.000 |
| P: | 3,15 | :PRO | 99.36 % | 1.000 |
| E: | 4, 7 | :GLU | 95.67 % | 1.000 |
| Q: | 9,11 | :GLN | 61.92 % | 1.000 |

Average AA Repetitive Yield     86.34 %

Combined AA Repetitive Yield     91.29 %     0.347

Theoretical Initial Yield:     6.67 pmol ( 13.35% )

FIG. 11

```
1  ..........................DRPERNEFQXQDGK..............  14
   						      ||.|||||.||||
1  MGPWGWKLRWTVALLLAAAGTAVGDRCERNEFQCQDGKCISYKWVCDGSA  50
```

FIG. 15A

```
    GCAGTGGGCGACAGATGTGAAAGAAAACGAGTTCCAGTGCCAAGACGGGAAATGCATCTCCTACAAGTGGTCTGCGATGCAGGCGCTGAGTGCCAGGAT
    AlaValGlyAspArgCysGluArgAsnGluPheGlnCysGlnAspGlyLysCysIleSerTyrLysTrpValCysAspGlySerAlaGluCysGlnAsp
1                                10                                 20                                30

TGCATTCCTCAGTTCTGGAGGTGCGATGGCCAAGTGGACTGACGCTCAGACGAGCAAGGCTGTCCCCAAGACGTGTCCCAAGGACGTGTCCCAGGACGAGTTT
    CysIleProGlnPheTrpArgCysAspGlyGlnValAspCysAspAspGlyLysAspGluSerAspGluArgCysProLysThrCysSerGlnAspGluPhe
61                               70                                 80                                90

TCCTGCCCGGTGCTCACCTGTGGTCCCGCCAGCTTCCAGTGCAACAGTCCCACCTGCATCCCCGAGCTGTGGGCCTGCGACAACGACCCCGACTGCGAA
    SerCysProValLeuThrCysGlyProAlaSerPheGlnCysAsnSerProThrCysIleProGluLeuTrpAlaCysAspAsnAspProAspCysGlu
121                              130                                140                               150

TTCCACTGCCTAAGTGGGCGACTGCATCCACTCCAGTGCCGCCTGATGTGGCCCCAGGACCCAACAAGTTCAAGTGTCACAGCGGCGAATGCATCACCCTGGACAAA
    PheHisCysLeuSerGlyArgLeuHisSerSerTrpArgCysAspGlyProAspCysLysAspLysSerAspGluGluAsnCysHisSerGlyGluCysIleThrLeuAspLys
181                              190                                200                               210

AAGGACATGAGCGATGAAGTTGGCTGCGTTAATGTGACACTCTGCGAGGGACCCAACAAGTTCAAGTGTCACAGCGGCGAATGCATCACCCTGGACAAA
    LysAspMetSerAspGluValGlyCysValAsnValThrLeuCysGluGlyProAsnLysPheLysCysHisSerGlyGluCysIleThrLeuAspLys
241                              250                                260                               270

AACGGCGGCTGTTCCCACGTCTGCAATGACCTTAAGATCGGCTACCGAGCAGGCTTCCAGTGCCCCGACGGCTTCCAGGGCCGAAGATGCGAAGAT
    AsnGlyGlyCysSerHisValCysAsnAspLeuLysIleGlyTyrGluCysLeuCysProAspGlyPheGlnLeuAlaGlnArgArgCysGluAsp
301                              310                                320                               330

GGCTTCCAGCTGGACCCCCACACGAAGCCTGCAAGGCCTCCACCCTTCTTCTTCACCAACCGGCACAGCAGAGTTCAGGAAGATGACGCTG
    GlyPheGlnLeuAspProHisThrLysAlaCysLysAlaSerThrPheThrAsnArgHisArgGluValArgLysMetThrLeu
361                              370                                380                               390

TACTGGTCTGACCTGTCCCAGAGAATGATCTGCAGACACCCAGCCCACGGCGTCTCTTCCTATGACACCGTCATCAGGACGACATCCAG
    TyrTrpSerAspLeuSerGlnArgMetIleCysArgAlaHisGlyValSerSerTyrAspThrValIleSerArgAspIleGln
```

```
    1
-13 AGAGGCTGGCGAGCATGGGGCCCTGGGGCTGGAAATTGCCTGACCGTCGCCTCCTCGCCGGGCGGGGACT    63
                      MetGlyProTrpGlyTrpLysLeuArgTrpThrValAlaLeuLeuLeuAlaAlaGlyThr
                        -20                                               -10               -1

GGCTCTGATGAGTCCCAGGAGACGTGCTTGTCTGTCACCTGCAAATCCGGGAGCTTCAGCTGTGGGGGCCCTGTCAACCGC    243
GlySerAspGluSerGlnGluThrCysLeuSerValThrCysLysSerGlyGluPheSerCysGlyGlyArgValAsnArg
                         40                                 50                                60

CGCTGCCACGATGGGAAGTGCATCTCTCGGCAGTTCCTCTGTGACTGTGAAGACCGGGACTGTCTTGACGGCTCAGACGAGCC    423
ArgCysHisAspGlyLysCysIleSerArgGlnPheValCysAspSerAspArgAspCysLeuAspGlySerAspGluAla
                         80                      90                   100                     120

GATGGCTCGATGAGTGGCCCGCAGCGCTGTAGGGGTCTTTACGTGTTCCAAGGGACAGTAGCCCCTGCTCGGCCTTCGAG    603
AspGlySerAspGluTrpProGlnArgCysArgGlyLeuTyrValPheGlnGlyAspSerSerProCysSerAlaPheGlu
                    140                     150                     160                       180

ACCTGCCCTGCCGAATTCCAGTGCTCTGATGAACTCCATGGCAGCCAGTGTGACCGGGAATATGACTGC    783
ThrCysProAlaGluPheGlnCysSerAspGluLeuHisGlySerArgGlnCysIleHisGlySerArgGlnCysIleHisGlySerArgGlnCysIleAspArgGluTyrAspCys
                    200                     210                  220                    230           240

GTCTGCAACATGGCTAGAGACTGGCCGGGACTGGTCAGAGAAGACCATCAAAGAGTGCGGGACCAACGAATGCTTGGACAAC    963
ValCysAsnMetAlaArgAspTrpProGlyLeuValArgGluAspHisGlnArgValArgAspGlnAsnGluCysLeuAspAsn
                    260                     270                  280                    290           300

ATCGATGAGTGTCAGGATGTGCCAGATCCCGACACCTGCGCAGCCAGCTCTGAGGAACCTGGTGGCTACAAGTGCCAGTGTGAGGAA    1143
IleAspGluCysGlnAspProAspThrCysGlnLeuValAsnLeuGluLeuGlyTyrLysCysGlnCysGluGlu
                    320                     330                     340                        360

GACCGGGAGCAGTACACCACCGCCTCATCCCCAACCTGGTCGCTGTTCGCTCTGGACGAACGTGGTGCCAGCAGAATGCG    1323
AspArgSerGluTyrThrSerLeuIleProAsnLeuArgAsnLeuArgAsnArgValAlaAlaSerAsnArgIle
                    380                     390                     400                        420

GCCCCCGACGGGCTCCTGTGGATCCGAATCCTACTGACCACTCTGTCCACTGGGCACTCCTCTCTGTTCG    1503
AlaProAspGlyLeuLeuAlaLysIleHisSerAsnIleTyrTrpThrAspSerValLeuGlyThrValSerValAla
                    440                     450                     460                        480

GACTGGGGAACTCCCGCCAAGATCAACAGAAAGGGGCCTGAATGGTGTGGACATTCTACTGACTGGTGACTGAAAACATTCAG    1683
AspTrpGlyThrProAlaLysIleLysGlyLeuAsnGlyValAspIleHisSerLeuTyrSerLeuAsnIleGln
```

```
     430                    440                    450
421  GATACCAAGGGCGTGAAGAGAAAACGTTATTCAGGGAGAACGGCTCCAAGCCAAGGGCCATCCTCGTTGGTGATCCTGTTCATGGCTTCATGTACTGACT
     AspThrLysGlyValLysThrLeuPheArgGluAsnGlySerLysProArgAlaIleValAlaSerProValHisGlyPheMetTyrTrpThr 490                    500                    510
481  TGGCCCAATGGCATCACCCTAGATCTCCTCAGTGGCCGCCTCTACTGGTTGACTCCAAACTTCACTCCATTCAAGCATCGATGTCAATGGGGCAAC
     TrpProAsnGlyIleThrLeuAspLeuLeuSerGlyArgLeuTyrTrpLeuAspSerLysPheLeuHisSerIleSerSerIleAspValAsnGlyGlyAsn 550                    560                    570
541  GATATCATCAACGAAGCCATTTCAGTGCCAACCGCCTCACAGTTCCGATGTCAACTTGTTGGCTGAAAACCTACTGTCCCCAGAGATATGGTCCTC
     AspIleIleAsnGluAlaIlePheSerAlaAsnArgLeuThrGlySerAspValAsnLeuLeuAlaGluAsnLeuLeuSerProGluAspMetValLeu 610                    620                    630
601  CTCCCCTGCCCCGAGATCAACCCCCACTCGCCCAAGTTACCTGCCCTGCCCGACGGCATGCTGCTGGCCAGGGACATGAGGAGCTGCCTCACAGAG
     LeuProAlaProGlnIleAsnProHisSerProLysPheThrCysAlaCysProAspGlyMetLeuLeuAlaArgAspMetArgSerCysLeuThrGlu 670                    680                    690
661  ACCACCCGGCCTGTTCCCGACACCTCCCGGCTCCCGGCCTTAAGAACATCAACAGCATCAACTTTGACAACCCCGTCTATCAGAAGACCACAGAGGAT
     ThrThrArgProValProAspThrSerArgLeuProGlyAlaThrGlyLeuThrThrValGluIleValThrMetSerHisGlnAlaLeuGlyAsp 730                    740                    750
721  CTTTGCCTGGGGTCTTCCTTCTATGGAAGAACTGGCGGCTTAAGAACATCAACAGCATCAACTTTGACAACCCCGTCTATCAGAAGACCACAGAGGAT
     LeuCysLeuValPheLeuLeuValPheArgLeuLysAsnTrpArgLeuLysAsnIleAsnSerIleAsnPheAspAsnProValTyrGlnLysThrThrGluAsp 790                    800                    810
781  ACAATCTGCCTGGAGTCCCCGCCCCTTCCTGTGAAGGATAAGAGAGAAAACAGGCCCGGGGACCAGGATGACACCTCCATTTCTCCAGAAGTTTTGAGTTTCTCCACC

TGGTTGTCTTCCTTTCCTGTGAAGGATAAGAGAGAAACAGGCCCGGGGACCAGGATGACACCTCCATTTCTCCAGAAGTTTTGAGTTTCTCCACC

GCAGATGGCACCAACGGGACCCCCTGCCCTCCATCCACCAATCTCTAAGCCAAACCCTAAACTCAGAGTCAACGTGTTTACCTCTTCTATGCA

TACCTTCCTTAAGCCAGGAAGGATTCATGGCGTCGGAAATGATCGCTGAATGCCGAAACTCATTCACCAAATGATGCCAC
```

```
                    520                    530                    540
CGGAAGAGACCATCTTGGAGGATGAAAAGAGGCTGCCCACCCCTTCTCTTGGCCGTCTTTGAGGACAAAGTATTTTGGACA    1863
ArgLysThrIleLeuGluAspGluLysArgLeuProThrProPheSerLeuAlaValPheGluAspLysValPheTrpThr
                    580                                           600
TTCCAACCTCACCCAGCCAAGAGAGTGAACTGGTGTGAGAGGACCACCCTGAGCAATGGCGGCTGCCAGTATCTGTGC      2043
PheHisLeuThrGlnProArgGlyValAlaSnTrpCysGluArgThrThrLeuSerAsnGlyGlyCysGlnTyrLeuCys
                    640                                           660
GCTGAGGCTGCAGTGGCCACCCAGGAGACATCCAGGTCAGCTAAAGGTCAGCTCCACAGCCGTAAGGACACAGCACACA    2223
AlaGluAlaAlaValAlaThrGlnGluThrSerSerThrValArgLeuLysValSerSerThrAlaValArgThrGlnHisThr
                    700                    710                    720
GTTGCTGCAGAGGAAATGAGAAGAAGCCCAGTAGCGTGAGGGCTCTGTCCATTGTCCTCCCCATCGTGCTCCTCGTCTTC    2403
ValAlaGlyArgGlyLysLysProSerSerValArgAlaLeuSerIleValLeuProIleValLeuLeuValPhe
                    760                                           780
GAGGTCCACATTTGCCACAACCAGACGGCTACAGTACCCCTGAGACAGATGGTCAGTCTGGAGGATGAGGTGGCCGTGA    2583
GluValHisIleCysHisAsnGlnAspGlyTyrSerTyrProSerArgGlnMetValSerLeuGluAspAspValAla***
                                           830
AGCTTTGTTTTATATTTATTCATCTGGGAGGCAGAACAGGCTTCGGACAGTGCCCATGCAATGCTGGGTTGGGATTT      2763

GTGACACAATCCTCAAACATGGAAGATGAAAGGGCAGGGGATGTCAGGCCCAGAGAACAAGTGGCTTCAACACACAACA    2943

AGCCTTGCTAGACAGCCAGGTTAGCCTTTGCCTGTCACCCCCGAATCATGACCCCAGTGTCTTTCGAGGTGGTTTG       3123

TTCCCAGAGGCAGAGCCTGAGTCACCGGTCACCCTTAAATATTTATTAAGTGCCTTACCTTGGCCGTGAG              3303

TCTCAGTTCAGAGTTGTACACTGTGTTGGCATTTGTTGTATTATTTGCACTGTTTTTCTGTCTGTGTGTGGGAT         3483

TGCCATTGTCGTCTCTTTATGTCCGCCAGTGCTTCCACTTCTATGCAAATGCCTCCAAGCCATTCACTTCCCAATCT      3663

TCATGAGGTCAGGAGATCGAGAGACCGTCGGCTAACAAGGTGAAACCCGTCTCTACTAAAATACAAAAATTAGCCGGG    3843

CACTGCGACTCCGAGTCGGGCCCTGGGGCGACAGAGACCCGTCTGAAAAAACAAAAACAAAAAAACCATGCATGG        4023
```

```
GACACGTGGCCTGCACCCAGGTGTGGCTGTCAGGACACCAGCTGCCCATCCTCCCGACCCTACCCACTTCCATTCCCGTGTCTCCTTGCACTT
GGGATCCCAGGCCAGGGAAAGCCCGTGTCAATGAATGCCGGGACAGAGAGGGCAGGTTGACCGGGACTTCAAAGCCGTGATCGTGAATATCGAGAAC
TGTCGTTGATGGGTATGTGTTTAAAACATGCACGGTGAGGCCGGCGCAGTGGCCTCACGCCCTGTAATCCCAGCACTTTGGGAGGCCGAGGCGGTGGA
CGCGGTGGTGGGCACCTGTGTGGGCTAGTCCCAGCTACTCGGGAGGCTGAGGCAGGAGAATGGTGTGAACCCGGGAAGCCTGCAGTGAGCCGAGATTGCGC
TGCATCAGCAGCCCATGGCCTCTGCCCAGGCATGGCCGAGGCTGAGGTGGGAGGATGGTTCAGGCTCAGGCATTTGAGGCTGCGTGAGCTATGATTATG
TGTAATCCCAGCACTTTGGGAGGCTGAGCTGGATCACTTGAGTTCAGGAGTTGGAGACCAGCCTGAGCAACAAAGCGAGATCCCATCCTACAAAAAC
TGAGCCCAGGAGGTGGAGGTTGCAGTGAGCCATGATCGAGCCACTGCAGATGAAGATGAAGACCCTATTCAGAAATACAACTATAAA
ATGTCCCGAGAGACAGTGACAGCCCTCCGTCAGACTCCCGGTGAACTGTTCACAGGGATTGGCAATTGTCCCCAGGACAAAACACTGTGTCCCCCC
TGTTTGCACTTTGTATATTGGTTGAAACTGTTATCACTTATATATATATACACACATATATAAAATCTATTATTTTTGCAAACCCTGGTTGCTG
TTTGCACGAACTGGACTGTGTGCAACGCTTTTTGGGAGAATGATGTCCCCGTTGTATGTATGAGTGGCTTCTGGGAGATGGGTGTCACTTTTTAAACCA
```

```
CCACTGCTTTCCAGCCTGGGCAACATAGTAAGACCCCATCTCTTAAAAAATGAATTTGGCCAGACACAGGTGCCTCACGCC    4203
CAAAAGTTAAAAATCAGCTGGGTGGCACGTGCCTGTGATCCCAGCTACTTGGGAGGCTGAGGCAGGAGGATCGCC          4383
AAAAATAAATAAATCCTCCAGTCTCTGGATCGTCTTTGACGGGACTTCAGGTTCTTTCTGAAATCGCCCGTGTTACTGTTGCACTG  4563
AGTGCAGGGAACCGTGATAAGCCTTTCTGGTTTCGGAGCACGTAAATGCGTCCCTGTACAGATAGTGGGATTTTTTGTTA    4743
TATTTGTTCAGTGACTATTCTCGGGGCCCTGTGTAGGGGTTATTGCCTCTGAAATGCCTCTTCTTTATGTACAAAGATTA    4923
CTGTATAGAAGGTTTTTGTAGCCTGAATGTCTTACTGTGATCAATTAAATTTCTTAAATGAAAAAAAAAAAA$_N$        5103
```

FIG. 19

```
    1........10........20........30........40........50
...MGPWGWKLRWTVALLLAAAGTAVGDRCERNEFQCQDGKCISYKWVCDGSA......Pre-LDLR
                         |||  ||||| |||  ||
                         DRXERNEFQXQDGK XI........sLDLR
                         1........10........
```

METHOD OF ANTIVIRAL USE OF SOLUBLE LDL RECEPTOR

CROSS-REFERENCE TO RELATED APPLICATIONS

The present application is a divisional of U.S. application Ser. No. 08/092,817, filed Jul. 19, 1993, now U.S. Pat. No. 5,496,926, which is a continuation-in-part of U.S. application Ser. No. 08/004,863, filed Jan. 19, 1993, now abandoned, the entire contents of which are hereby incorporated herein by reference.

BACKGROUND OF THE INVENTION

1. Field of the Invention

The present invention relates to the soluble low density lipoprotein (LDL) receptor, to its production and to pharmaceutical compositions containing it.

2. Description of the Background Art

Interferons (IFN) are inducible proteins that are produced by various cells and induce an antiviral state in animal cells. There are three major types of IFNs, distinguished by their antigenic properties: α, β and γ. IFN-α and IFN-β are related proteins of 166 or 165 amino acid residues that are induced by viruses or nucleic acids and are produced by cells from various tissues, including immune cells. IFN-γ is a protein of 130–143 amino acid residues which is produced by mitogen-activated T-cells and by large granular lymphocytes. The production of IFN is usually transient and it stops shortly after the inducer disappears. For a recent review of these issues, see Taylor S. L. and Grossberg S. E., 1990, Virus Research, 15, 1–26.

In addition to the three well-characterized types of interferons, there are several reports describing partially characterized species of interferons. A group of IFN-α-like (IFN-α1) genes and pseudogenes, also known as class II IFN-α or IFN-omega was discovered and reported (Revel, M., 1984, in "Antiviral Drugs and Interferon: The Molecular Basis of their Activity", Y. Becker (ed.), Martinus Neijhoff Publ., Boston, pp. 357–434; Capon, D. J. et al., 1985, Molec. Cell. Biol., 5, 768–779; Hauptmann, R. and Swetly, P., 1985, Nuc. Acid. Res., 13, 4739–4749). These are virus-induced interferons having about 172 amino acid residues which are present in the natural mixture of human IFN-α produced by leukocytes (Adolf., G. R., 1990, Virology, 175, 410–417).

Treatment of human peripheral blood mononuclear leukocytes with a mitogen resulted in production of IFN-γ and a novel IFN-like substance named IFN-δ (Wilkinson, M. and Morris, A., 1983, Biochem. Biophys. Res. Comm. 111, 498–503). IFN-δ was found to be acid resistant and active only on human fibroblasts having chromosome-21 trisomy and not on WISH cells. It was antigenically distinct from the three known IFN types.

Acid-labile alpha-interferons were described in several publications. An acid-labile IFN-α was induced in cultures of lymphocytes from individuals who have recently received influenza vaccine, by stimulation in vitro with the influenza virus (Balkwill, F. R. et al, 1983, J. Exp. Med., 157, 1059–1063). This type of IFN was neutralized by anti-IFN-α serum and was active on Mandin Darby Bovine Kidney (MDBK) cells. The presence of such acid-labile alpha-type IFN in sera of patients with systemic lupus erythematosus was reported (Klippel, J. H. et al, 1985, Annals Rheum. Disease, 44, 104–108). An acid-labile IFN-α was produced similarly to IFN-α by Sendai virus induction of human peripheral leukocytes (Matsuoka, H. et al., 1985, J. Gen. Virol., 66, 2491–2494). Acid-labile IFN-α was spontaneously produced in cultures of peripheral blood mononuclear cells (Fischer, D. G. and Rubinstein, M., 1983, Cellular Immunology, 81, 426–434).

Another type of IFN, called IFN-epsilon, was produced by epithelial cells exposed to virus. It was produced together with IFN-β but was active on epithelial cells and not on other cell types (Jarvis, A. P. and Kosowsky, D. I., 1984, U.S. Pat. No. 4,614,651).

Among other cytokines, TNF, IL-6 and IL-1 were reported to exhibit antiviral activity (Mestan, J. et al., 1986, Nature, 323, 816–819; Wong, G. H. W. and Goedell, D., 1986, Nature, 323, 819–822; Billiau, A., 1987, Antiviral Research, 8, 55–70). TNF is produced only by immune cells and it was suggested that IL-1 and TNF exert their antiviral activity by inducing the production of IFN-β (Billiau, A., op. cit.).

Several interferon-induced proteins have been identified and some of them were shown to be instrumental in the induction of the antiviral state by IFNs. The best studied one is (2'–5') oligo adenylate synthetase, an intracellular enzyme which polymerizes ATP into pp(A2'–5'p)nA, where n is preferably 2 or 3, but may be as long as 15 (Kerr, I. M. and Brown, R. E., 1978, Proc. Natl. Acad. Sci. USA, 75, 256–260). Such oligomers activate a latent ribonuclease (RNASE-F) which degrades ribosomal RNA and polysomes, thereby inhibiting viral and cellular protein synthesis. Mother IFN-induced intracellular enzyme is a 2'–5'; phosphodiesterase which may remove the CCA terminus of tRNA, thereby leading to inhibition of protein synthesis (Schmidt, A. et al., 1979, Proc. Natl. Acad. Sci. USA, 76, 4788–4792). A third known IFN-induced intracellular enzyme is a 70 Kd protein kinase which phosphorylates the Initiation Factor eIF-2, thereby leading to inhibition of the initiation of mRNA translation into proteins (Ohtsuki, K. et al., 1980, Nature, 287, 65–67).

Other IFN-induced intracellular proteins include the nuclear IFN-Responsive Factors (IRF-1 and IRF-2) which regulate IFN-responsive genes; metallothionein, a 56 Kd protein of unknown function in the IFN-induced antiviral state; Factor B of the alternative complement system and the murine Mx gene product, which is responsible for resistance to influenza (Reviewed in Taylor, I. L. and Grossberg, S. E., 1990, Virus Research, 15, 1–26). Other IFN-induced cell associated polypeptides were identified on 2-D gels following IFN treatment and [$^{35}$S]-methionine pulsing, but these proteins were not further characterized in terms of their structure and function (Weil, J. et al., 1983, Nature, 301, 437–439). Several cell surface interferon-induced proteins were identified, including class I and II MHC antigens, IgG, Fc receptor and cytoskeletal components (Reviewed in Revel, M., 1984, in "Antiviral Drugs and Interferons: The Molecular Basis of their Activity", Y. Becker (ed.), pp. 357–434, Martinus Neijhoff Publ., Boston).

Additional IFN-induced proteins that were secreted into the medium have been disclosed in the literature, such as β2-microglobulin, a shedded component of the cell-surface class I MHC antigens (Dolei, A. F. et al., 1981, Antiviral Res., 1, 367–373), and plasminogen activator and lymphotoxin, which were induced in lymphocytes by IFN (Jones, C. M. et al., 1982, J. Interferon Res., 2, 377–386; Wallach, D. and Hahn, T., 1983, Cellular Immunol., 76, 390–396). IFN-γ-treated monocytes released TNF which enhanced the overall antiviral effect (Gerrard, T. et al., 1989, J. Interferon Res., 9, 115–124). IFN-γ-induced proteins of molecular weight 30,000 (extracellular) and 25,000

(intracellular) were described (Luster A. D. et al., 1988, J. Biol. Chem., 263, 12036–12043), but their role was not determined.

Although many IFN-induced proteins have been disclosed, none of them is related to a soluble LDL receptor. The existence of a soluble LDL receptor as a separate protein has not been so far disclosed. The full size low density lipoprotein receptor (LDLR) is a transmembrane glycoprotein which is not soluble in the absence of detergents. It consists of 839 amino acid residues and exhibits a molecular weight of 164,000. Its only known function is to internalize LDL and VLDL. Structurally it consists of several domains, some of which are shared with other proteins. The N-terminal ligand-binding domain is made of 292 amino acid residues arranged in 7 cysteine-rich imperfect repeats. This domain is followed by a region homologous to the EGF precursor (400 amino acid residues), a region of 58 amino acid residues rich in O-linked sugars, a single transmembrane domain of 22 amino acid residues and a cytoplasmic domain of 50 amino acid residues (Schneider W. J. et al., J. Biol. Chem. 257, 2664–2673, 1982; Yamamoto T. et al., Cell 39, 27–38, 1984). However, there is no mention of antiviral properties of the LDL receptor. The predicted nucleotide sequence (SEQ ID NO:3) of the cDNA corresponding to the LDL receptor in the mRNA, including the predicted LDL receptor amino acid sequence (SEQ ID NO:4) encoded thereby, according to Yamamoto et al (supra) is presented in FIG. 15.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It has been found that when human fibroblasts or epithelial cells are treated with an interferon, a protein showing antiviral activity is produced and accumulates in the supernatant of the cell cultures. This protein has now been purified to homogeneity and was identified as the soluble extracellular region of LDL receptor.

The present invention thus provides a soluble LDL new receptor protein consisting essentially of at least one replication of the soluble portion of an LDL receptor, or a mutein, fused protein, salt, functional derivative and/or active fraction thereof. The antiviral activity of the receptor protein may be conveniently determined, for example, in a system consisting of WISH amnion cells and vesicular stomatitis virus (VSV) as a challenge.

The invention also provides a soluble LDL receptor corresponding to the extracellular portion (750 amino acid residues) of the LDL receptor, which is purified to homogeneity with respect to proteinaceous impurities.

The invention relates especially to the soluble LDL receptor comprising at least, but not exclusively, the ligand binding domain of the mature LDL receptor, and, more specifically, corresponding at least to amino acid residue 4 to 292–350 of SEQ ID No:4 or any range therein, such as at about amino acid residue 3B of the mature LDL receptor, corresponding to amino acid residues 25 to 313–371 of SEQ ID No:4, or any range therein, such as amino acid residues 25–313 of the LDLR precursor sequence. The C-terminus of a soluble LDL receptor is expected to be between amino acids 292 and 350 of the mature LDL receptor protein, or 313–371 of the LDLR precursor, such as any value therein.

The invention also relates to a soluble LDL receptor, including the amino acid sequence substantially as shown in FIG. 10.

In another aspect, the invention relates to a process for the preparation of the soluble LDL receptor, comprising treatment of suitable cells with an interferon, isolation of the soluble LDL receptor from the supernatant and purification thereof.

The invention further concerns recombinant DNA molecules comprising the nucleotide sequence coding for said protein or for its active muteins or fused proteins, expression vehicles comprising them and host cells transformed therewith and to a process for producing the soluble LDL receptor, its active muteins or fused proteins, by culturing said transformant cells in a suitable culture medium.

The soluble LDL receptor of the invention, its active muteins, fused proteins, and their salts, functional derivatives and active fractions, are for use as active ingredients of pharmaceutical compositions to protect mammals against viral infections.

The present invention also relates to methods for treating cells in mammals against viral infection by administration of an anti-viral effective amount of a pharmaceutical composition comprising a soluble LDL receptor protein of the present invention.

The present invention also relates to naturally occurring soluble LDL receptor. Such soluble LDL receptors can be purified and/or isolated from biological fluid samples, such as urine.

The invention also relates to methods for purifying soluble LDL receptor from biological fluid samples comprising isolation and/or purification of soluble LDL receptors from concentrated and/or filtered biological samples containing a soluble LDL receptor.

BRIEF DESCRIPTION OF THE FIGURES

FIG. 10 shows the original output of the protein microsequencer. Fractions 10–12 of RP-HPLC (FIG. 7) 0.4 ml each, were pooled, concentrated by ultrafiltration and the resulting sample (1 μg) was subjected to protein microsequence analysis. The N-terminal 15 amino acid residues (SEQ ID NO:1) found in this manner are shown.

FIG. 11 shows the computer output of the search for the sequence obtained by the protein microsequencer shown in FIG. 10. Amino acids 1–14 of SEQ ID NO:1 are compared to the N-terminal 50 amino acids of the human LDL receptor (SEQ ID NO:2).

FIGS. 15A–15F show the nucleotide sequence (SEQ ID NO:3) of the cDNA corresponding to the LDL receptor mRNA and the predicted amino acid sequence (SEQ ID NO:4) of the protein, as presented in FIG. 6 of Yamamoto et al., Cell 39:27–38 (1984), at page 31, which article is hereby entirely incorporated herein by reference.

FIG. 19 shows a comparison between the sequence of urinary soluble LDL receptor (SEQ ID NO:5) and the known sequence of the first 50 N-terminal residues of the precursor-LDL receptor (SEQ ID NO:2). Residues 1–21 of SEQ ID NO:2 of the precursor-LDL receptor are the signal peptide. Residues 22–24 of SEQ ID NO:2 are missing in mature soluble LDL receptor, e.g., as presented in FIG. 15.

DETAILED DESCRIPTION OF THE PREFERRED EMBODIMENTS

Figure 1:
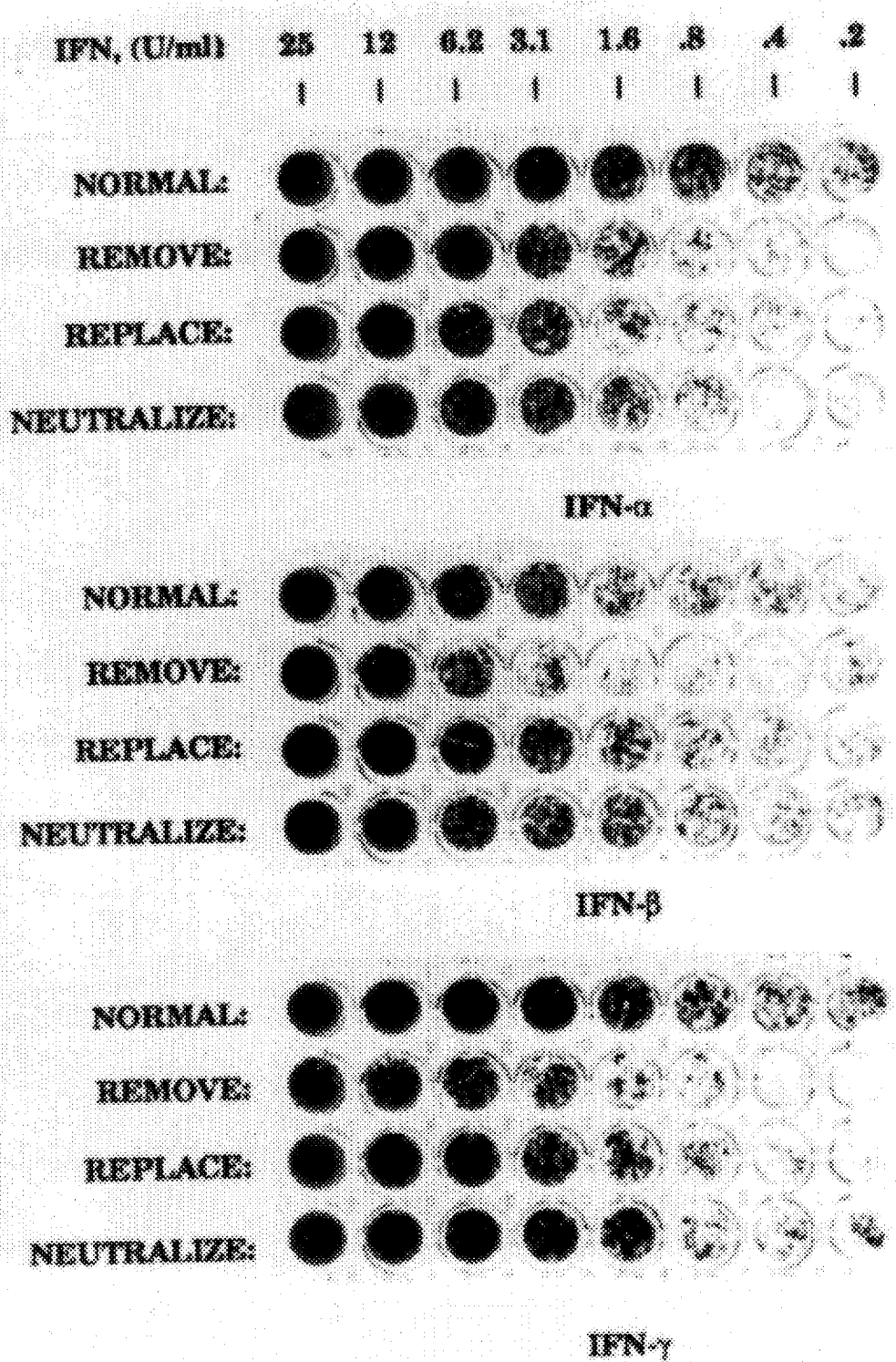
FIG. 1 shows evidence for the existence of antiviral activity which is not the added interferon. The protective effect of various interferons against the cytopathic effect of vesicular stomatitis virus (VSV) on human amnion WISH cells, is determined under a variety of conditions. The assay was performed in 96-well plates and each row represents a serial two-fold dilution of IFN. The final concentration of IEN in the first column from left is 25 IU/ml. The medium in rows 1, 5, and 9 (from the top) was not removed. The medium in rows 2, 6 and 10 was aspirated, the cell monolayers were washed once and fresh medium was added. In rows 3, 7 and 11 the medium was replaced with fresh dilutions of the respective IFNs, and in rows 4, 8 and 12, neutralizing antibodies specific to IFN-α, IFN-β and to IFN-γ were added, respectively. VSV in growth medium was applied to the cells in all wells. The infected cultures were further incubated overnight and then stained with crystal violet, in order to better evaluate visually the extent of the virus cytopathic effect.

It has been found that interferon-treated cells secrete into the culture medium an antivirally active protein which is not an interferon. This protein is not neutralized by antibodies directed against any of the three types of human interferons (both NIH standards and neutralizing monoclonal antibodies). The protein was identified as comprising the extracellular ligand binding domain of the LDL receptor.

The soluble LDL receptor is secreted into the culture medium by mammalian cells that enter into an antiviral state in response to any interferon. Examples are fibroblast cells or epithelial cells derived from amniotic fluid, e.g. U cells, WISH cells. It also can be found in the urine of healthy human individuals.

In contrast to interferons, the soluble LDL receptor does not induce in the cells an antiviral state, but is antiviral by itself. Thus, cells treated simultaneously with the soluble LDL receptor and virus will not lyse, while cells treated with virus alone or simultaneously with virus and IFN-γ, will be infected and lyse after 12 hours. This shows that IFN-γ gives no immediate protection to the cells against virus since it takes about 10 hours until the antiviral state is established in cells treated with IFN-γ. In contrast, the soluble LDL receptor protects the cells immediately when added to them.

When examined by size exclusion chromatography, the soluble LDL receptor has an apparent molecular weight of about 40,000.

For the production of the soluble LDL receptor, suitable cells grown in culture are treated with an IFN in a suitable medium and then incubated for some hours at 37° C., thus producing the soluble LDL receptor which is secreted into the medium and can be isolated from the supernatant. Suitable cells are those which enter into an antiviral state in response to an interferon. Similar results were obtained with IFN-α, IFN-β and IFN-γ, but IFN-γ is preferably used because it does not exhibit antiviral activity under the conditions of the antiviral assay for the soluble LDL receptor (simultaneous addition of the soluble LDL receptor and challenge virus to the cell culture).

In a preferred embodiment of the invention, human WISH cells are treated with IFN-γ in MEM supplemented with a serum substitute and then further incubated at 37° C. The highest titer of the soluble LDL receptor was obtained after 17 hours. The supernatant of the cells containing the soluble LDL receptor is then harvested and concentrated by known methods, such as by ultrafiltration or by dialysis against semi-solid polyethylene glycol 20,000. The concentrated supernatant is then purified by chromatographic procedures.

In a preferred embodiment, purified soluble LDL receptor may be produced by a process comprising the following steps:

(a) growing human WISH cells in culture to confluency, inducing the cells with 30 U/ml IFN-γ in a serum-free medium and, after about 17 hours, harvesting the culture supernatant;

(b) concentrating said supernatant about 30-fold by, e.g., ultrafiltration with a membrane of molecular weight cut-off of about 10,000;

(c) subjecting said concentrated supernatant of step (b) to anion exchange chromatography to obtain partially purified active fractions of the antiviral factor;

(d) applying said partially purified fraction from step (c) to chromatography on a hydroxyapatite column to obtain partially purified fractions of the antiviral factor;

(e) applying said partially purified fraction from step (d) to anion exchange HPLC to obtain partially purified fractions of the antiviral factor;

(f) applying said partially purified fractions from step (e) to hydrophobic interaction chromatography to obtain partially purified fractions of the antiviral factor; and (g) applying said partially purified active fractions from step (f) to reversed phase high pressure liquid chromatography (HPLC) at about neutral pH to obtain partially purified antiviral factor. This step is then repeated to obtain homogeneous antiviral factor, defined by its ability to inhibit the cytopathic effect (CPE) exerted by vesicular stomatitis virus (VSV) on human WISH cells.

The ion exchange chromatography of step (c) is preferably performed on a TSK-DEAE column (Tosoh Corp., Japan) at pH about 8 eluted with increasing salt concentration. The hydroxyapatite chromatography is preferably performed on a Biogel HTP column (BioRad, USA) at pH 6.8 with phosphate buffers as eluants. The anion exchange HPLC is preferably performed on a SUPERFORMANCE TMAE column in a manner similar to the TSK-DEAE step. The hydrophobic interaction chromatography is preferably performed on a phenyl sepharose column eluted with decreasing salt concentration. The reversed phase HPLC is preferably performed on an AQUAPORE RP300 column, at Ph 7.5, with a gradient of acetonitrile.

In another preferred embodiment soluble LDL receptor is purified by a process comprising at least steps (a), (b) and (c) as described in the aforementioned embodiment and then performing a step of immunoaffinity chromatography on a column of a monoclonal antibody directed against the soluble LDL receptor.

The monoclonal antibody can preferably be the one made by hybridoma C7 (ATCC, CRL 1691). The partially purified soluble LDL receptor is loaded onto the columns at neutral pH, the column is washed with 0.5M NaCl at neutral pH and the soluble LDL receptor is eluted in an enhanced state of purity with 50 mM $Na_2CO_3$ (pH 11) and immediately neutralized.

Preferably, in all steps of the purification the chromatography is monitored by measuring the protein concentration (absorbance at 280 nm or relative fluorescence following "on-line" reaction of representative aliquots with flourescamine). The antiviral activity in each fraction is determined by inhibition of the VSV-induced CPE in WISH cells according to the bioassay described herein.

In another preferred embodiment, soluble LDL receptor can be purified from the urine of healthy, human individuals. It may also be found in other biological fluids, such as blood serum, lymph, cerebral spinal fluid, saliva, and fractions thereof. The method of isolating and/or purifying soluble LDL receptor from a biological fluid may include a process comprising at least one of the above steps (b)–(g), wherein at least one of steps (b)–(g) may be replaced by affinity chromatography using monoclonal antibodies specific for an epitope of a soluble LDL receptor protein.

Alternatively, isolation and/or purification of soluble LDL receptor from biological samples, such as urine, may comprise (1) concentrating the fluid sample by microfiltration and/or ultrafiltration; (2) affinity chromatography using monoclonal antibodies specific for soluble LDL receptor; (3) reverse phase HPLC; and/or optionally, (4) size exclusion chromatography; in order to isolate the soluble LDL receptor, which protein does not naturally occur isolated from other naturally occuring proteins. In the above method, step (4) is optional, since the fraction obtained after the reverse phase HPLC step maybe of sufficient purity.

In the above alternative isolation and purification method of soluble LDL receptor from a biological fluid sample, it is preferred that the biological fluid sample be subjected to microfiltration using a pore size of 0.45 micron or smaller, such as 0.4, 0.3, 0.25, 0.2, or 0.1 microns. Additionally, it is preferred that the biological sample be additionally or alternatively subjected to ultrafiltration using a molecular weight cutoff selected from the group consisting of 70K, 60K, 50K, 40K, 30K, 20K, 10K and/or 5K.

In a preferred embodiment, monoclonal antibodies used in the affinity chromatography step (2) may be specific for a soluble portion of an LDL receptor, as presented herein. In a preferred embodiment, the monoclonal antibody is cross reactive with a monoclonal antibody produced by hybridoma C7 (ATCC, CRL 1691).

In the affinity chromatography step (3) it is preferred that the partially purified soluble LDL receptor be loaded onto the column(s) at neutral pH, the column be washed with 0.5M NaCl at neutral pH, and the soluble LDL receptor eluted in an enhanced state of purity with 50 mM $Na_2CO_3$ (pH 11) and immediately neutralized, such as with an acid, such as with 3M acetic acid.

It is also preferred that the resulting fractions in the above step be tested for antiviral activity, as presented herein wherein the fractions containing the highest activities are used for the next purification and/or isolation step. The antiviral activity may be determined, for example, by showing inhibition of cytopathic effect (CPE) asserted by vesicular stomatitis virus (VSV) on human WISH cells.

In another preferred embodiment, in the RP-HPLC step (3), the column(s) are preferably preequilibrated with 20 mM Hepes buffer at pH 7.5 and the column is then washed and the protein eluted by using an acetonitrile gradient in the same buffer. In one preferred embodiment, the antiviral activity is eluted or in the range of 10–20% acetonitrile, such as 12–18, 13–15, and 14–16% acetonitrile, wherein 14% is preferred. Antiviral active fractions may then preferably be tested and collected for further purification or sequencing.

In another preferred embodiment, optional step (4) as size exclusion chromatography, the soluble LDL receptor-containing fraction from a biological fluid is mixed with larger proteins, such as at least one selected from the group consisting of bovine serum albumen (BSA), human immunoglobulin, and carbonic anhydrate in phosphate buffered saline (PBS). The resulting mixture is used as the sample to be applied to the size exclusion chromatography column under near physiological conditions. The human immunoglobulin, BSA and carbonic anhydrate are used as molecular weight markers. Preferrably the antiviral activity eluted peak has an apparent molecular weight of 25–35 Kda, such as 26–34, 26–33, 26–32, 27–31, or about 27–30 KDa molecular weight, as determined according to size exclusion chromatography or SDS PAGE, (under reducing or nonreducing conditions).

Preferably in all steps of the purification, the LDL receptor protein containing fractions are monitored by measuring the protein-concentration, e.g., absorbance at 280 nm or relative fluorescence following "on-line" reaction of representative aliquots with flourescamine. The antiviral activity in each fraction is also determined by inhibition of VSV induced CPE WISH cells, according to known method steps, e.g., as described herein.

LDL receptor protein-containing fractions from the RP-HPLC step, or further following size exclusion chromatography step, can be used according to known method steps, to provide purified LDL receptor protein in sequencable form, which can then be sequenced, according to the present invention. In a preferred embodiment, the LDL receptor fractions are absorbed on a PVDF membrane and subjected to microsequence analysis on a protein microsequencer, as commercially available, and/or is known to those skilled in the art.

As used herein the term "muteins" refers to analogues of the soluble LDL receptor in which one or more of the amino acid residues of the natural soluble LDL receptor, preferably 1–10 and more preferably 1–5 residues or even only a single residue, are replaced by different amino acid residues or are deleted, or one or more amino acid residues, such as 1–10, 1–5 or only one residue are added to the natural sequence of the soluble LDL receptor, without changing considerably the antiviral activity of the resulting product. These muteins are prepared by known synthesis and/or site-directed mutagenesis techniques, or any other known technique suitable therefor. The substitutions are preferably conservative. See, e.g., Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference.

The types of such substitutions which may be made in the protein or peptide molecule of the present invention may be based on analysis of the frequencies of amino acid changes between a homologous protein of different species, such as those presented in Table 1–2 of Schulz et al. (supra) and FIGS. 3–9 of Creighton (supra). Based on such an analysis, conservative substitutions may be defined herein as exchanges within one of the following five groups:

1. Small aliphatic, nonpolar or slightly polar residues: ala, ser, thr (pro, gly);

2. Polar, negatively charged residues and their amides: asp, asn, glu, gln;

3. Polar, positively charged residues: his, arg, lys;

4. Large aliphatic, nonpolar residues: met, leu, ile, val (cys); and

5. Large aromatic residues: phe, tyr, trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note that Schulz et al. would merge Groups 1 and 2, above. Note also that Tyr, because of its hydrogen bonding potential, has some kinship with Ser, Thr, etc.

Conservative amino acid substitutions according to the present invention, e.g., as presented above, are known in the art and would be expected to maintain biological and structural properties of the polypeptide after amino acid substitution. Most deletions and insertions, and substitutions according to the present invention are those which do not produce radical changes in the characteristics of the protein or peptide molecule. One skilled in the art will appreciate that the effect of substitutions can be evaluated by routine screening assays, either immunoassays or bioassays. For example, a mutant typically is made by site-specific mutagenesis of the peptide molecule-encoding nucleic acid, expression of the mutant nucleic acid in recombinant cell culture, and, optionally, purification from the cell culture, or a biological sample containing a soluble LDL receptor protein, for example, by immunoaffinity chromatography using a specific antibody on a column (to absorb the mutant by binding to at least one epitope).

The term "fused protein" refers to a polypeptide comprising the soluble LDL receptor or a mutein thereof fused with another protein which has an extended residence time in body fluids. The soluble LDL receptor may thus be fused to another protein, polypeptide or the like, e.g., an immunoglobulin or a fragment thereof.

The term "salts" herein refers to both salts of carboxyl groups and to acid addition salts of amino groups of the soluble LDL receptor, muteins and fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein cover derivatives of the soluble LDL receptor and its fused proteins and muteins, which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it. These derivatives may, for example, include polyethylene glycol side-chains which may mask antigenic sites and extend the residence of the soluble LDL receptor in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or acyl derivatives of free hydroxyl groups (for example that of seryl or threonyl residues) formed with acyl moieties. The term "functional derivative" also includes proteins which have an amino acid sequence longer or shorter than the sequence determined, as long as the protein still has the ability to inhibit viral infection.

As "active fractions" of the soluble LDL receptor, its fused proteins and its muteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has the ability to inhibit viral infection and/or activity. Such active fractions can be readily determined by testing smaller and smaller portions of the entire soluble LDL receptor or mutein to find the smallest fragment which retains the ability to inhibit viral infections. Any fractions containing the smallest active fraction will also be an active fraction. Undue experimentation would not be involved as the required tests for antiviral activity (as described herein) may be routinely carried out.

This invention further concerns DNA molecules comprising the nucleotide sequence encoding the soluble LDL receptor, fused proteins, muteins or active fractions thereof, replicable expression vehicles containing said DNA molecules, hosts transformed therewith and protein produced by expression of such transformed hosts. The term "DNA molecules" includes genomic DNA, cDNA, synthetic DNA and combinations thereof.

The production of the recombinant soluble LDL receptor may be carried out by different techniques. According to one approach, the known cDNA of the entire human LDL receptor is taken from plasmid pLDLR-2 (Yamamoto et al., op cit.). The DNA is subjected to site directed mutagenesis with appropriate oligonucleotides so that a termination codon and a polyadenylation site are inserted after codon 292 of the mature LDL receptor. This construct is then inserted into appropriately constructed expression vectors by techniques well known in the art (see Maniatis et al., op cit.). Double-stranded cDNA is linked to plasmid vector by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

The production of a fused protein comprising the ligand binding domain of the LDL receptor and, e.g., the constant region of $IgG_2$ heavy chain may be carried out as follows: the DNA of pLDLR is subjected to site-directed mutagenesis with appropriate oligonucleotides so that a unique restriction site is introduced immediately after codon 292 of the mature LDL receptor. A plasmid bearing the constant region of $IgG_2$ heavy chain, e.g., $pRKCO4_2Fc_1$ (Byrn R. A. et al., 1990 Nature (London) 344, 667–670) is subjected to similar site-directed mutagenesis to introduce the same unique restriction site as close as possible to Asp 216 of $IgG_1$ heavy chain in a way that allows translation in phase of the fused protein. A dsDNA fragment consisting of 5' untranslated sequences and encoding the leader and about the first 295 amino acids of LDL receptor is prepared by digestion of the mutated pLDL receptor at the EcoRI and the unique restriction sites. The mutated $pRKCD4_2Fc_1$ is similarly digested to generate a large fragment containing the plasmid and the $IgG_1$ sequences. The two fragments are then ligated to generate a new plasmid encoding a polypeptide consisting of about the N-terminal 295 acids of LDL receptor and about 227 C-terminal amino acids of $IgG_1$ heavy chain (hinge region and CH2 and CH3 domains). The DNA encoding the fused protein may be isolated from the plasmid by digestion with Eco RI and then inserted into an efficient expression vector.

In order to be capable of expressing the soluble LDL receptor, its muteins or the fused proteins, an expression vector should comprise also specific nucleotide sequences containing transcriptional and translational regulator information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage lambda, the bla promoter of the β-lactamase gene of pBR322, and the CAT promoter of the chloramphenicol acetyl transferase gene of pPR325, etc., or inducible, such as the prokaryotic promoters including the major right and left promoters of bacteriophage lambda ($P_l$ and $P_r$), the trp, recA, lacZ, lacI, ompF and gal promoters of E. coli, or the trp-lac hybrid promoter, etc. (Glick, B. R. (1987) J. Ind. Microbiol. 1:277–282).

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence SD sequence) appropriately positioned from the initiation codon and complementary to the 3'-terminal sequence of 16S RNA.

For eukaryotic hosts, different transcriptional and translational regulator sequences may be employed, depending on the nature of the host. They may be derived from vital sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the soluble LDL receptor of the invention or its fragments or muteins or fused proteins thereof, and the operably linked transcriptional and translational regulator signals is inserted into a vector which is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototropy to an auxotrophic host, biocide resistance, e.g., antibiotics, or heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., (1983) Mol. Cel. Biol. 3:280.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in E. coli, for example, pBR322, ColE1, pSC101, pACYC 184, etc. (see Maniatis et al., op. cit.); Bacillus plasmids such as pC194, pC221, pT127, etc. (Gryczan, T., "The Molecular Biology of the Bacilli", Academic Press NY (1982), pp. 307–329); Streptomyces plasmids including pIJ101 (Kendall, K. J. et al., (1987) J. Bacterial. 169:4177–4183); Streptomyces bacteriophages such as φC31 (Chater, K F. et al., in "Sixth International Symposium on Actinomycetales Biology", Akademiai Kaido, Budapest, Hungary (1986), pp. 45–54), and Preudomonas plasmids (John, J. F., et al. (1986) Rev. Infect. Dis. 8:693–704), and Izaki, K. (1978) Jpn. J. Bacterial. 33:729–742).

Preferred eukaryotic plasmids include BPV, vaccinia, SV40, 2-micron circle, etc., or their derivatives. Such plasmids are well known in the art (Botstein, D., et al. (1982) Miami Wint. Symp. 19:265–274; Broach, J R., in "The Molecular Biology of the Yeast Saccharomyces: Life Cycle and Inheritance", Cold Spring Harbor Laboratory, Cold Spring Harbor, N.Y., pp. 445-470 (1981); Broach, J. R., (1982) Cell 28:203-204; Bollon, D. P., et al. (1980) J. Clin. Hematol. Oncol. 10:39-48; Maniatis, T., in "Cell Biology: A Comprehensive Treatise, Vol. 3: Gene Expression," Academic Press, N.Y., pp. 563-608 (1980)).

Once the vector or DNA sequence containing the construct(s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as E. coli, Bacillus, Streptomyces, Pseudomonas, Salmonella, Serratia, etc. The most preferred prokaryotic host is E. coli. Bacterial hosts of particular interest include E. coli K12 strain 294 (ATCC 31446), E. coli X1776 (ATCC 31537), E. coli W3110 (F-, lambda-, prototrophic (ATCC 27325)), and other enterobacterium such as Salmonella typhimurium or Serratia marcescens and various Pseudomonas species. Under such conditions, the protein will not be glycosylated. The prokaryotic host must be compatible with the replicon and control sequences in the expression plasmid.

However, since the soluble LDL receptor is a cysteine rich protein, eukaryotic hosts are preferred over prokaryotic hosts. Preferred eukaryotic hosts are mammalian cells, e.g., human, monkey, mouse and chinese hamster ovary (CHO) cells, because they provide post-translational modifications to protein molecules including correct folding, correct disulfide bond formation as well as glycosylation at correct sites. Also yeast cells and insect cells can carry out post-translational peptide modifications including high mannose glycosylation. A number of recombinant DNA strategies exist which utilize strong promoter sequences and high copy number of plasmids which can be utilized for production of the desired proteins in yeast and in insect cells. Yeast cells recognize leader sequences on cloned mammalian gene products and secrete peptides bearing leader sequences.

After the introduction of the vector, the host cells are grown in a selective medium, which selects for the growth of vector-containing cells. Expression of the cloned gene sequence(s) results in the production of the soluble LDL receptor, a fusion protein, or a mutein or a fragment thereof. The expressed protein is then isolated and purified by any conventional procedure involving extraction, precipitation, chromatography, electrophoresis, or the like, or by affinity chromatography, using anti-soluble LDL receptor monoclonal antibodies (e.g., hybridoma C7, Belsiegel U. et al., J. Biol. Chem., 256:11923-11931, 1981) immobilized on a gel matrix contained within a column. Crude preparations containing said recombinant soluble LDL receptor are passed through the column whereby the soluble LDL receptor will be bound to the column by the specific antibody while the impurities will pass through. After washing, the protein is eluted from the gel at a high pH, e.g., pH 11.

The soluble LDL receptor and its muteins, fused proteins and their salts, functional derivatives, and active fractions thereof are indicated for the treatment of viral diseases in mammals.

The present invention further relates to pharmaceutical compositions comprising a pharmaceutically acceptable carrier and the soluble LDL receptor of the invention or its active muteins, fused proteins and their salts, functional derivatives or active fractions thereof, either as the sole active ingredient or in combination with other antiviral agents, e.g., interferons. These compositions may be used against viral diseases. The way of administration can be via any of the accepted modes of administration for similar agents and will depend on the condition to be treated, e.g., intravenously or intramuscularly or subcutaneously, in case of systemic viremia, or local injection or topical application in case of a localized infection, or continuously by infusion, etc.

The pharmaceutical compositions of the invention are prepared for administration by mixing the soluble LDL receptor its derivatives, alone or together with other antiviral agents, with physiologically acceptable carriers, stabilizers and excipients, and prepared in dosage form, e.g., by lyophilization in dosage vials. The amount of active compound to be administered will depend on the route of administration, the disease to be treated and the condition of the patient. Local injection, for instance, will require a lower amount of the protein on a body weight basis than will intravenous infusion in case of systemic viremia.

Effective amounts of a soluble LDL receptor protein or composition, are from about 0.01 µg to about 100 mg/kg body weight, and preferably from about 10 µg to about 50 mg/kg body weight, such as 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg. See, e.g., Berkow et al, eds., The Merck Manual, 16th edition, Merck and Co., Rahway, N. J., 1992; Goodman et al., eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Col, Boston, (1985), Katzung, Basic and Clinical Phamacology, Appleton and Lange, Norwalk, Conn., (1992), which references and references cited therein, are entirely incorporated herein by reference.

The invention will now be illustrated by the following non-limiting examples.

EXAMPLES

Example 1

Preliminary Identification of the Antiviral Activity of the Soluble LDL Receptor The presence of an unknown antiviral factor in the supernatant of IFN-induced cells was shown by several experiments.

The antiviral effect was determined by the virus cytopathic effect (CPE) reduction assay (Rubinstein, S. et al (1981) J. Virol. 37:755-758) using human WISH cells and VSV as a challenge. Initial studies were performed with IFN-α, IFN-β and IFN-γ and similar results were obtained with all three IFNs.

In the experiment described in FIG. 1, and summarized in Table 1, human amnion WISH cells (ATCC CCL-25) were seeded in a 96-well microtiter plate. A few hours later, serial twofold dilutions (from right to left), starting with 50 U/ml of IFN-α, IFN-β and IFN-γ in MEM (Minimal Essential Medium) supplemented with 10% fetal bovine serum, were applied to monolayers of the cells in rows (from top) 1-3, 4-6 and 7-9, respectively, and the cells were incubated overnight at 37° C. The medium in rows 1, 5 and 9 was not removed. The medium in rows 2, 6 and 10 was aspirated, the cell monolayers were washed once and fresh medium was added. In rows 3, 7 and 11, the medium was replaced with fresh dilutions of the respective IFNs, and in rows 4, 8 and 12, neutralizing antibodies specific to IFN-α, IFN-β (NIH standards) and to IFN-γ (monoclonal antibody 166.5, described in Novick et al., (1983) EMBO 3(2), p. 1527) were added respectively. VSV in growth medium was applied to the cells in all wells. The infected cultures were further incubated overnight and then stained with crystal violet, in order to better evaluate visually the extent of the virus cytopathic effect.

TABLE 1

The role of antiviral factor in IFN action

| Row of FIG. 1 | Treatment[1] | 50% CPE dilution | units/ ml[2] | % of activity |
|---|---|---|---|---|
| 1 | IFN-α 24 hrs, standard assay | 400 | 1000 | 100 |
| 2 | IFN-α 24 hrs, wash | 100 | 250 | 25 |
| 3 | IFN-α 24 hrs, replace IFN | 200 | 250 | 25 |
| 4 | IFN-α 24 hrs, neutralize | 300 | 375 | 37 |
| 5 | IFN-β 24 hrs, standard assay | 400 | 1000 | 100 |
| 6 | IFN-β 24 hrs, wash | 200 | 500 | 50 |
| 7 | IFN-β 24 hrs, replace IFN | 400 | 1000 | 100 |
| 8 | IFN-β 24 hrs, neutralize | 400 | 1000 | 100 |
| 9 | IFN-γ 24 hrs, standard assay | 800 | 1000 | 100 |
| 10 | IFN-γ 24 hrs, wash | 200 | 250 | 25 |
| 11 | IFN-γ 24 hrs, replace IFN | 400 | 500 | 50 |
| 12 | IFN-γ 24 hrs, neutralize | 800 | 1000 | 100 |

[1] In the standard assay, (rows 1, 5 and 9) IFN was added in serial twofold dilutions (from right to left in FIG. 1) to monolayers of WISH cells in 96-well plates. After 24 hrs, VSV was added and 18 hrs later the cells were fixed and stained. In other cases, washing (rows 2, 6 and 10), replacement with IFN in fresh medium (rows 3, 7 and 11) or addition of anti-IFN neutralizing antibodies (rows 4, 8 and 12), were done immediately prior to challenge with VSV.
[2] The titers of IFN standards (rows 1, 5 and 9) were designated as 1000 U/ml.

The dilutions at which NIH standard IFNs (rows 1, 5 and 9) gave 50% CPE were first determined. As seen in FIG. 1, rows 2, 6 and 10, washing off the cells after 24 hrs and prior to VSV challenge, significantly reduced the potency of all three IFNs. Replacement of the medium with fresh dilutions of IFN reduced the level of protection with IFN-α (row 3) and IFN-γ (row 1), but not with IFN-β (row 7). Addition of neutralizing anti-IFN antibodies to the growth medium after 24 hrs exposure to IFN, had only a small effect on the activity of IFN-α (row 4) and no effect on the activity of IFN-β and IFN-γ (rows 8 and 12, respectively).

Since IFNs induce antiviral state in cells after interaction with specific cell surface receptors, they can be removed once the antiviral state is established and the cells will remain protected against the virus. Therefore, removal of IFN after the antiviral state was established, is not expected to affect the apparent IFN potency. However, in the above experiment, it was shown that the apparent antiviral potency of a given IFN sample was significantly lower if the culture medium was replaced prior to challenge with virus (rows 2, 6 and 10). Even if the medium was replaced with fresh IFN, both in the case of IFN-α (row 3) and IFN-γ (row 11) the level of protection was lower than without replacement. Hence the culture medium had a non interferon component that protects the cells from virus infection.

Incubation of the cells after application of IFN and addition of anti-IFN neutralizing antibodies prior to virus challenge without replacement of the growth medium, lowered the antiviral activity of the IFN-α only slightly (row 4) and not the activity of IFN-β or IFN-γ (rows 8 and 12, respectively). These results suggest that the reduced activity observed when the IFN-containing medium was removed, is not due to removal of the IFN molecules, but rather to removal of other molecules which are required to achieve full antiviral protection.

The antiviral enhancing activity in the medium, was herein demonstrated in vitro in the IFN CPE reduction assay. It is possible that the active extracellular component, plays also a role in vivo in the IFN antiviral activity. When IFN is used in a systemic disease where secreted components are eliminated continuously, administration of such a factor might greatly enhance the effect of IFN.

Example 2

Production and Purification of the Antiviral Protein 2.1 Production of Crude Antiviral Protein Human amnion cells WISH (ATCC CCL-25) were grown to confluency on FIBRACELL discs (Sterilin, U.K.) in spinner flasks, in a medium consisting of MEM supplemented with 10% fetal calf serum (FCS). At confluency, the medium was discarded and the discs washed several times with serum-free MEM. The cells were then incubated in MEM (1.3 1) supplemented with a protein-free serum substitute ADC-1 (1:50, Biological Industries, Beit Haemek, Israel), Hepes 20 mM, Insulin 0.2 μg/ml and IFN-γ (30 U/ml). Incubation was continued for 17 hrs at 37° C. The culture medium was then collected, spun (5000×g, 15 min) and the supernatant was collected and kept under sterile conditions at 4° C. for short periods (up to 24 hrs), or at −20° C. until used. The cell culture could be continuously used for production by adding more protein-free medium and IFN-γ.

2.2 Concentration of Crude Antiviral Factor

The antiviral factor can be concentrated either by dialysis against polyethylene glycol 20,000 or by ultrafiltration. Crude cell supernatant (1.5 1) of step 2.1 above was concentrated about 30-fold by ultrafiltration in a MINITAN unit (Millipore, USA) with a polysulfone membrane of molecular weight 10,000 cut off (PTGC MINITAN plate). The crude retentate was washed with sodium borate buffer, 20 mM, pH 8 (Buffer A) and brought to a volume of about 50 ml. This material was used immediately or kept frozen at −20° C. until used.

2.3 Chromatography on TSK-DEAE

Figure 2:
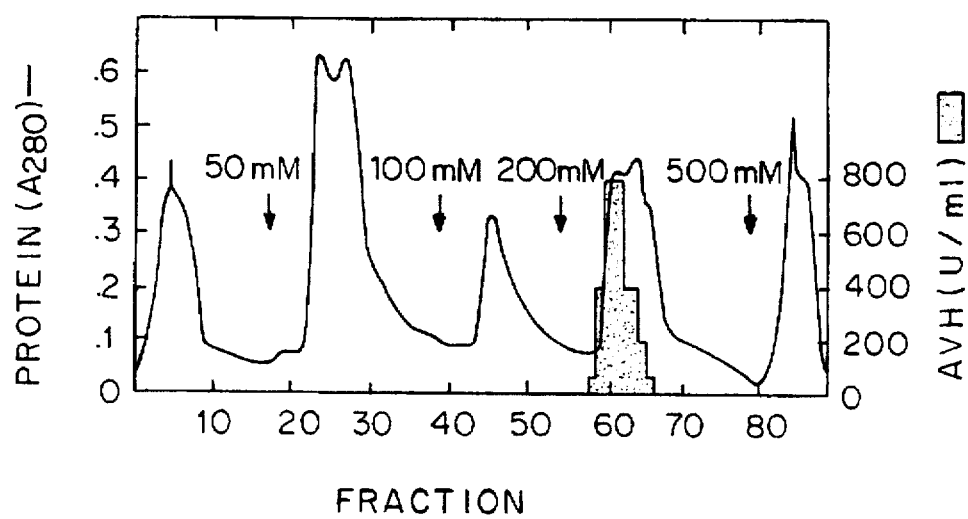
FIG. 2 shows the elution pattern of the proteins and antiviral activity from a TSK-DEAE anion exchange column.

A TSK-DEAE column (2.5×33 cm, Tosoh, Japan) was equilibrated with Buffer A. Concentrated antiviral factor from MINITAN step 2.2 above was applied to the column at a flow rate of 8 ml/min. The column was then washed with Buffer A and eluted stepwise with 50, 100, 200 and 500 mM NaCl in Buffer A. Fractions of 12 ml were collected and subjected to bioassay. The column was monitored by absorbance at 280 nm (FIG. 2). The protein peak eluted with 200 mM NaCl, contained antiviral activity when tested in the presence of neutralizing anti IFN-γ monoclonal antibody No. 166-5. It was pooled and concentrated to a volume of about 20 ml by ultrafiltration on a YM-10 membrane (MW cut off 10,000, Amicon USA). The material was kept at −20° C. until used.

2.4 Hydroxyapatite Chromatography

Figure 3:
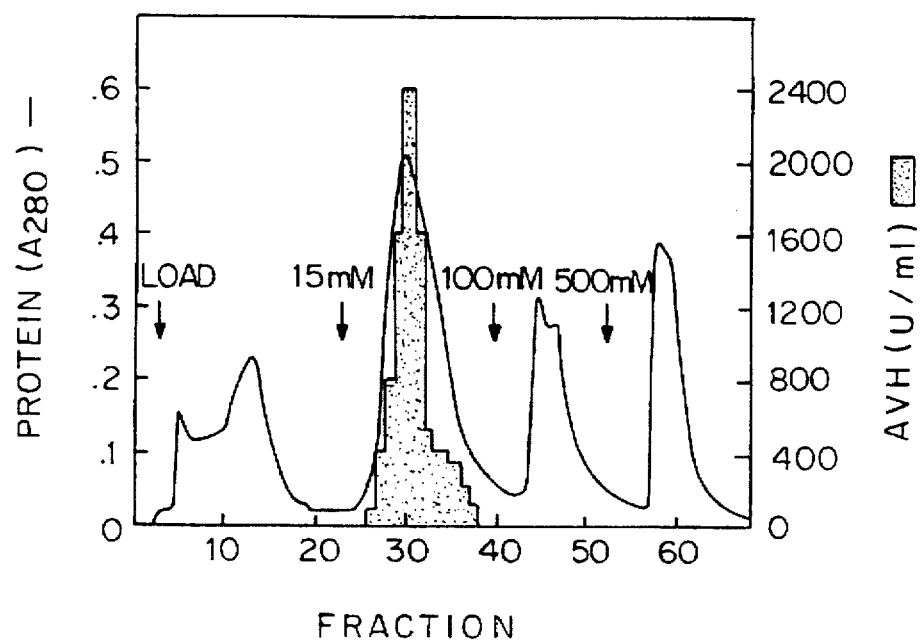
FIG. 3 shows the elution pattern of proteins and antiviral activity from a hydroxyapatite Biogel HTP column.

A hydroxyapatite biogel HTP column (2.5×4 cm, BioRod, USA) was equilibrated with water. The concentrated 0.2 m NaCl protein peak of step 2.3 (166 mg) was loaded on the Biogel HTP column at a flow rate of 2 ml/min. The column was washed with water and eluted with 15 mM sodium phosphate pH 6.8. Fractions of 2 ml were collected and tested for antiviral activity. The Column was monitored by absorbance at 280 nm (FIG. 3). The antiviral activity was found in the 15 mM phosphate eluate, pooled and concentrated by ultrafiltration.

2.5 Anion Exchange HPLC

Figure 4:
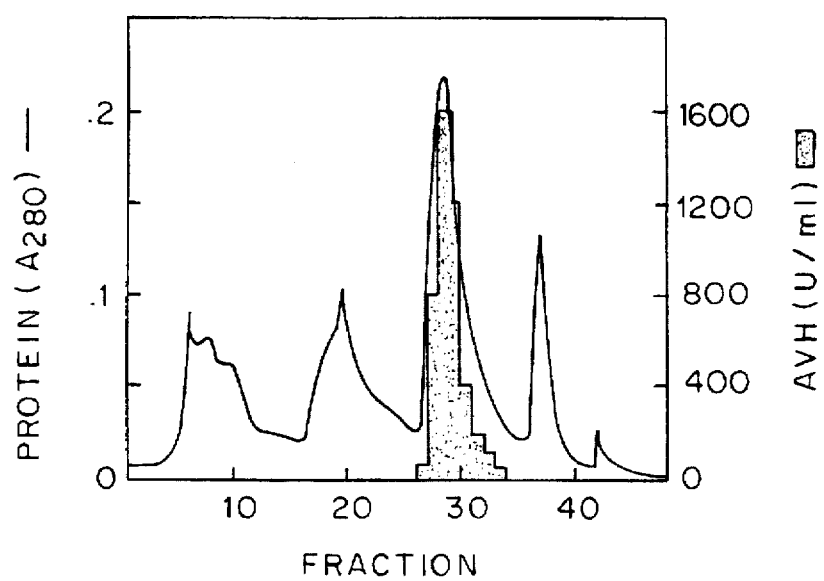
FIG. 4 shows the elution pattern of the proteins and antiviral activity from a SUPERFORMANCE TMAE-65-S anion exchange HPLC column.

An anion exchange HPLC column (SUPERFORMANCE-TMAE-650S, E. Merck, Germany) was pre-equilibrated with Buffer A. The concentrated pool containing 73 mg protein from step 2.4 was spun (10,000×g, 5 min.) and the supernatant was applied to the column at a flow rate of 1 ml/min. The column was washed with Buffer A and then eluted stepwise by 50, 100, 200 and 500 mM NaCl in Buffer A. Fractions of 2.5 ml were collected and assayed for antiviral activity. The column was monitored at 280 nm (FIG. 4). The activity eluted in the 200 mM NaCl fraction. This fraction was pooled and kept at −20° C. until used.

2.6 Hydrophobic Interaction Chromatography

Figure 5:
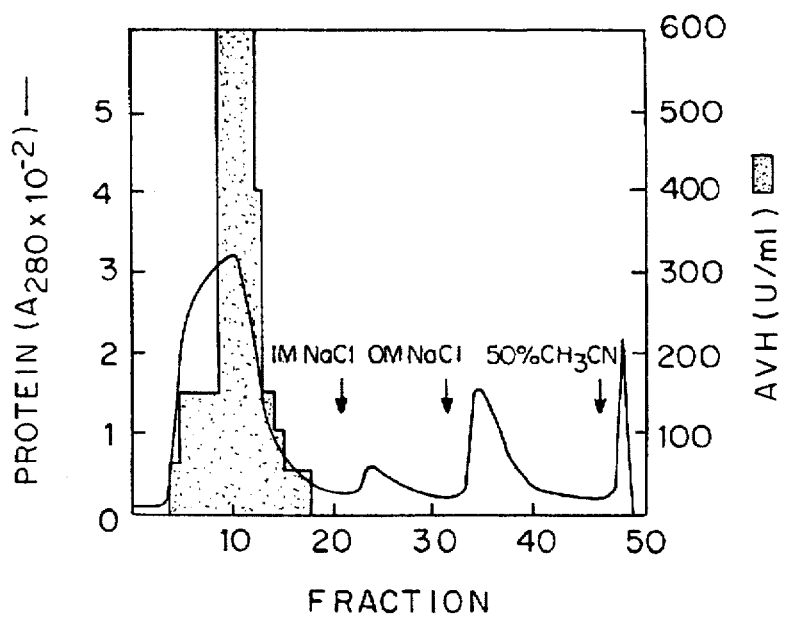
FIG. 5 shows the elution pattern of proteins and antiviral activity from a phenyl sepharose hydrophobic interaction column.

A phenyl sepharose column (1.5×6.5 cm, Pharmacia, Sweden) was equilibrated with 1.5M NaCl in Buffer A. The 200 mM Na phosphate protein peak of step 2.5 (10 mg) was brought to 1.5M NaCl and loaded (1 ml/min.) on the phenyl sepharose column. The column was washed with 1.5M NaCl in Buffer A and unbound protein peak was collected. The column was eluted stepwise with 1M NaCl in Buffer A, Buffer A and 50% $CH_3CN$/50% Buffer A. Antiviral activity was obtained in the unbound (1.5M NaCl) fraction. The column was monitored at 280 nM (FIG. 5).

2.7 Reversed Phase HPLC

Figure 6:
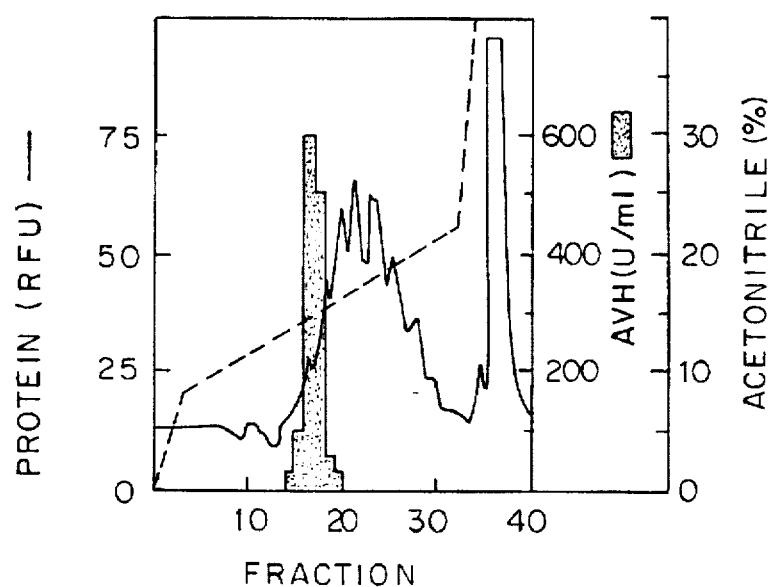
FIG. 6 shows the elution pattern of protein and antiviral activity from a reversed-phase AQUAPORE RP-300 HPLC column.

The unbound pooled fraction from step 2.6 (1.2 mg) was loaded on an AQUAPORE RP-300 RP-HPLC column (4.6× 30 mm) that was preequilibrated with 20 mM Hepes buffer pH 7.5. The column was washed and eluted at a flow rate of 0.5 ml/min by an acetonitrile gradient in the same buffer. Fractions of 1 ml were collected and tested for antiviral activity. The antiviral activity eluted at 14% acetonitrile and was associated with a protein peak. However, this peak was not completely resolved from adjacent peaks (FIG. 6). The column was monitored by a flourescamine-based post-column reaction system (Stein S. and Moschera J., 1981, Methods in Enzymology, 79:7–16).

Figure 7:
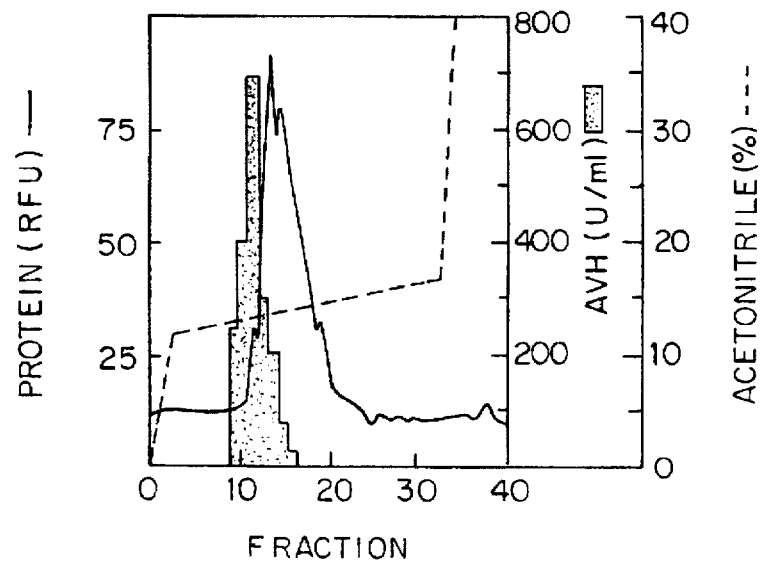
FIG. 7 shows the elution pattern of protein and antiviral activity from rechromatography on a reversed-phase HPLC column.
Figure 8:
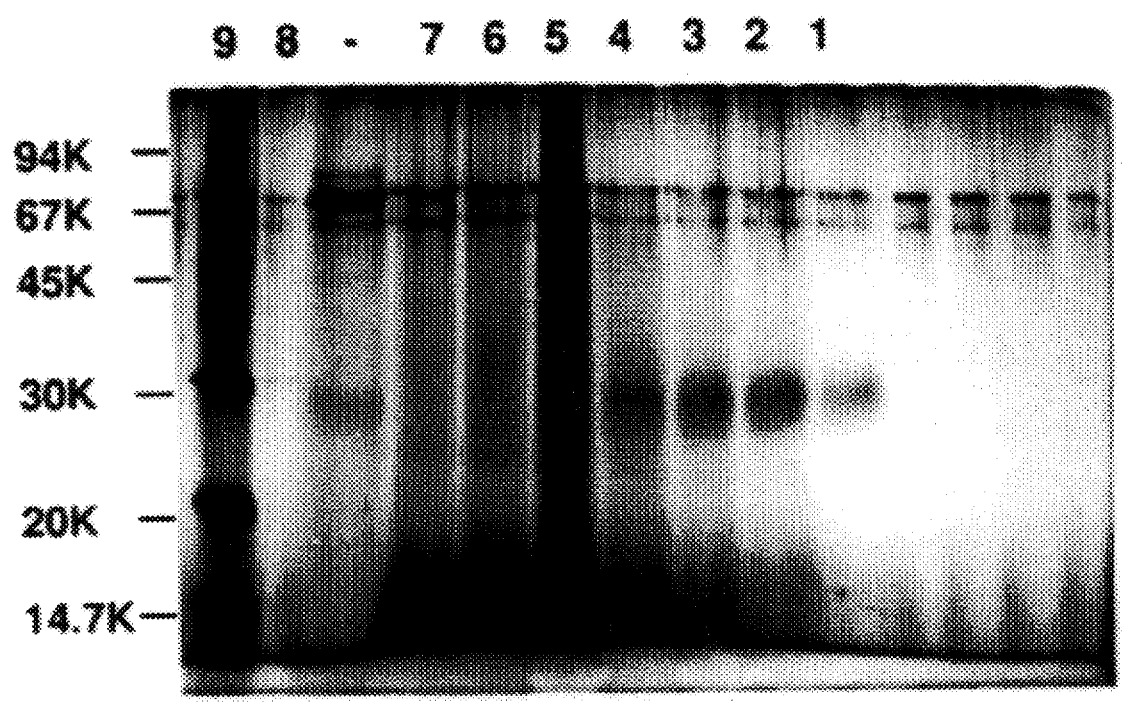
FIG. 8 shows sodium dodecyl sulfate-polyacrylamide gel electrophoretic (SDS-PAGE) analysis of various fractions obtained in the last step of the purification procedure. A 13% acrylamide gel was used and stained with silver. The lanes are: 1–7, aliquots (400 ul) of fractions 10–16 respectively from RP-300 chromatography (FIG. 7) which were concentrated by ultrafiltration; 8, control sample buffer; 9, molecular weight markers, indicated on the left side.

Active fractions (56 µg) were pooled, diluted twofold with 20 mM Hepes, pH 7.5 and rechromatographed on the AQUAPORE RP-300 column (FIG. 7). Aliquots (400 µl) of each fraction were concentrated by ultrafiltration and subjected to polyacrylamide (13%) gel electrophoresis in the presence of sodium dodecyl sulfate and β-mercaptoethanol (SDS-PAGE). The protein bands were visualized by silver staining. The lanes are: lane 1–7, fractions 10–16 respectively of the HPLC; lane 8, control sample buffer; lane 9, molecular weight markers, indicated on the left side (FIG. 8).

Example 3

Characterization of the Antiviral Factor 3.1 Bioassay of Antiviral Activity

The assay is similar to the cytopathic effect (CPE) inhibition assay which is used for measuring IFN activity (Rubinstein S. et al., (1981) J. Virol. 37: 755–758). The antiviral activity is calibrated against NIH reference standard of human IFN-β. It can also be calibrated with IFN-α standard, but not with IFN-γ, which does not protect the cells from virus under these assay conditions. The following procedure is used:

Confluent monolayers of WISH cells are prepared on day 1, seeding 45,000 cells/well in 100 µl of MEM supplemented with 10% FCS, in 96-flat bottom well plates. The plates are incubated at 37° C. in 5% $CO_2$. On day 2, samples of the antiviral factor are diluted twofold serially in a separate plate (100 µl). Neutralizing monoclonal anti-IFN-γ antibody (166-5) sufficient for neutralizing 1000 U/ml of IFN-γ is added to each well and the solutions are transferred to the plate with the WISH cells, followed immediately by challenge with an appropriate amount (see below) of stock VSV (50 µl). The plates are incubated overnight at 37° C. The assay is calibrated against standard IFN-β. On day 3, about 20 hours following virus challenge, the cytopathic effect in control wells is observed microscopically. When it is ≧80%, the plates are drained and the monolayer is stained with crystal violet (0.5% in 70% Aq. methanol), washed with plenty of tap water and the end points are determined by observation under the microscope. An appropriate amount of VSV for this assay is the dilution of stock VSV which, when added to a serial twofold dilution of standard IFN-β under the assay conditions, will give 50% CPE at IFN-β dilution of about 3–6 U/ml after 20–24 hrs of incubation.

3.2 The Antiviral Factor is a Protein

Three experiments were performed in order to demonstrate that the antiviral factor is a protein.

a. Molecular weight >10,000, as shown by the ability to concentrate the antiviral activity by dialysis against PEG 20,000 and by ultrafiltration on membranes with cut-off of 10,000 Da, indicating that the antiviral factor is a macro-molecule.

b. Heat lability. Active fraction from a MONO Q anion exchange step (same as step 2.5 of example 2) was heated in a 1000° C. bath for 10 min and then tested for antiviral activity. No activity remained following this treatment. See Table 2.

c. Trypsin sensitivity. Active fraction from the MONO Q anion exchange step was incubated with TPCK-treated trypsin (Worthington) at 5:1 protein:enzyme ratio, respectively, overnight at room temperature. Control fraction was similarly kept without trypsin and control trypsin was made as well. It was found that 66% of the antiviral activity was lost by trypsin treatment and hence, it was concluded that the antiviral factor is trypsin sensitive. See Table 2.

d. The antiviral factor is not an interferon. Interferon is defined as a protein which induces in cells an antiviral state which persists even after removal of the interferon. Cells were incubated with antiviral factor-containing medium from the MONO Q step for 24 hrs, the medium was removed, the cells were washed and challenged with VSV. No protection from VSV was observed. Hence it was concluded that the antiviral factor is not an interferon and its mechanism of action is different from that of an interferon.

e. The antiviral factor is probably not a degradative enzyme. The site and mode of action of the antiviral factor is still not known. In order to clarify these questions, further studies must be carried out with different viruses. One simple experiment was performed to test whether the factor is an enzyme that degrades viruses, e.g., a proteolytic enzyme. For this purpose, VSV was incubated with serial twofold dilutions of the factor for different time periods at 37° C. Bovine MDBK cells were then added to the wells and the extent of CPE was determined. It was found that VSV gave the same extent of CPE when mixed with the cells immediately after addition of the antiviral factor or when pre-incubated with the antiviral factor for 5 hrs at 37° C. Hence it was concluded that the antiviral factor is probably not a virus degrading enzyme.

TABLE 2

Sensitivity of the antiviral factor to heat and trypsin

| Sample | Activity U/ml | % |
| --- | --- | --- |
| Stock (MONO Q) antiviral factor, overnight, room temp. | 75 | 100 |
| Stock antiviral factor + trypsin, overnight room temp. | 25 | 33 |
| Stock antiviral factor (MONO Q), room temp., 10 min. | 65 | 100 |
| Stock antiviral factor, 100° C., 10 min. | 0 | 0 |

3.3 Size Exclusion Chromatography of the Antiviral Factor

Figure 9:
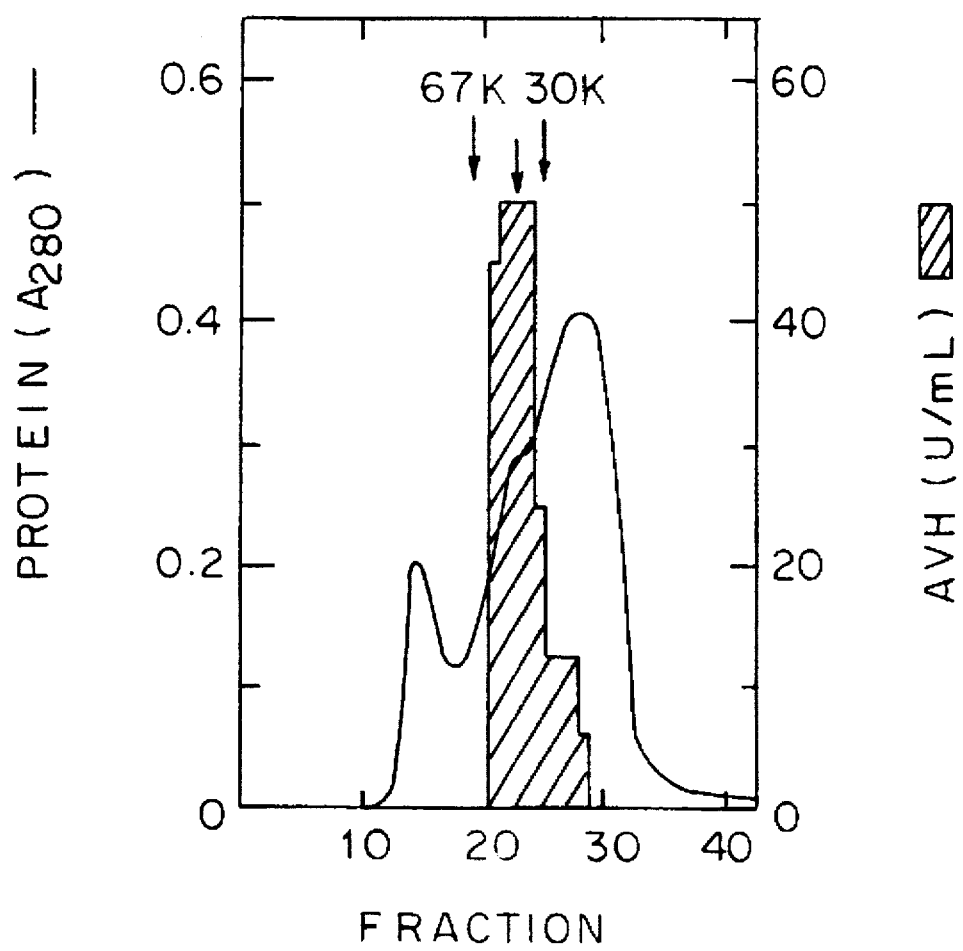
FIG. 9 shows the elution pattern of antiviral activity from a SUPEROSE 12 size exclusion HPLC column.

Antiviral factor from the TSK-DEAE step (0.4 ml) was fractionated on a size exclusion column (SUPEROSE 12, 1×30 cm, Pharmacia) in phosphate buffered saline under near physiological conditions. The column was pre-equilibrated and eluted with phosphate buffered saline at a flow rate of 0.5 ml/min. Fractions of 1 ml were collected and antiviral activity was measured in each fraction. The column was monitored at 280 nm (FIG. 9). The column was calibrated with bovine serum albumin (67K) and carbonic anhydrase (30K) as molecular weight markers. It was found that the antiviral activity eluted as a peak of apparent molecular weight 40,000. However, this peak was rather broad.

3.4 Species Specificity of the Antiviral Factor

The antiviral factor was found to be active on human WISH cells. It was also found to be active on bovine MDBK cells and murine L cells. Hence it was concluded that the factor is not species specific.

3.5 Protein Sequence Analysis and Identification of the Antiviral Factor

Aliquots (400 µl) of fractions 10–12 from the last RP-HPLC step (see 2.7 in example 2) were pooled, concentrated by ultrafiltration and the concentrate (0.5 µg) was subjected to microsequence analysis on model 475 protein microsequences (Applied Biosystems, USA). The resulting sequence of the N-terminal 15 amino acid residues (SEQ ID NO:1) as identified by this system is given in FIG. 10. The amino acid in cycle 10 was not identified while the Pro in cycle 3 and 15 was identified with relatively low confidence (given in Pmol ratio).

The resulting amino acid sequence (SEQ ID NO:1) was compared with NBRF protein databank and it gave 100% identity with the N-terminal sequence of the human low density lipoprotein (LDL) receptor (SEQ ID NO:2) starting at residue 25 of the precursor LDL receptor (residue 4 of mature LDL receptor). The amino acids in cycles 3, 10 and 15 were not intially identified due to the limitations of the sequencing method, but were later confirmed to be cysteine residues by homology with the mature LDL receptor sequence of FIG. 15 (SEQ ID NO:4). The identity between the isolated receptor and the known LDL receptor is shown in FIG. 11.

The soluble antiviral protein of the present invention has a molecular weight of between 29,000 or 40,000 according to the two methods that were used for its estimation. It is therefore concluded that the antiviral protein corresponds to the N-terminal cysteine-rich domain of the LDL receptor. According to Esser (Esser, V. et al. (1988) J. Biol. Chem. 263, 13282–13290) the cysteine-rich N-terminal domain of 292 amino acid residues is the ligand binding domain of LDL receptor and its calculated molecular weight is about 33,000–38,000 depending on the extent of glycosylation.

Example 4

Immunoaffinity Chromatography of the Antiviral Factor

Figure 12:
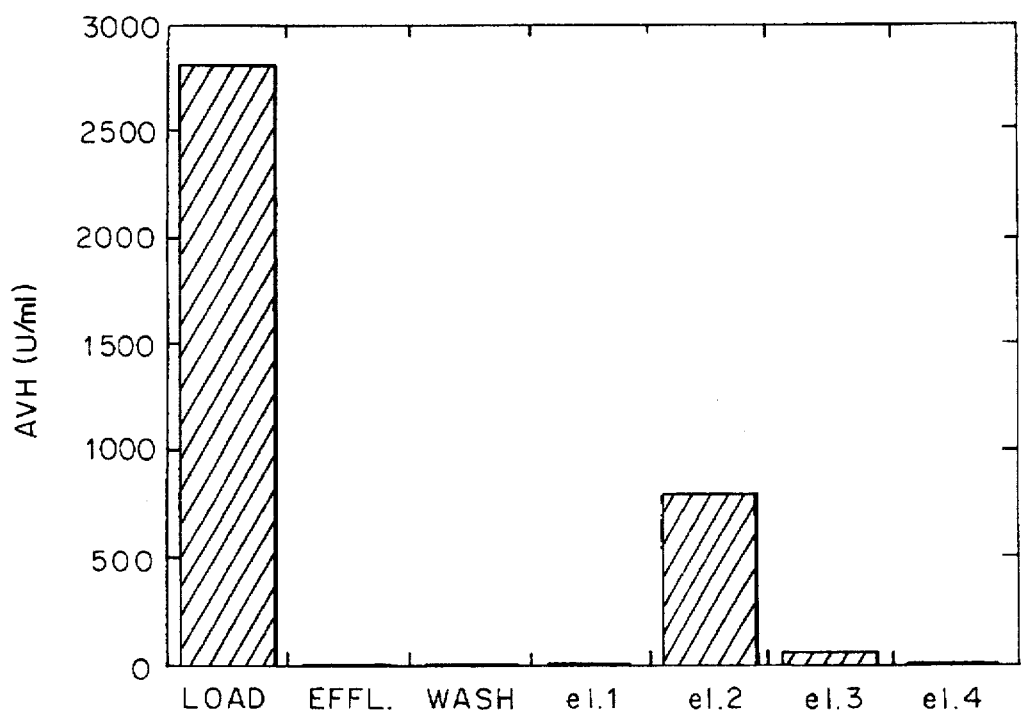
FIG. 12 shows the total antiviral activity of various fractions from the immunoaffinity chromatography of partially purified soluble LDL receptor on monoclonal antibody C7 column. The bars are: load-column load; effl.—effluent (unbound fraction); el.1–el.4—elutions 1–4.
Figure 13:
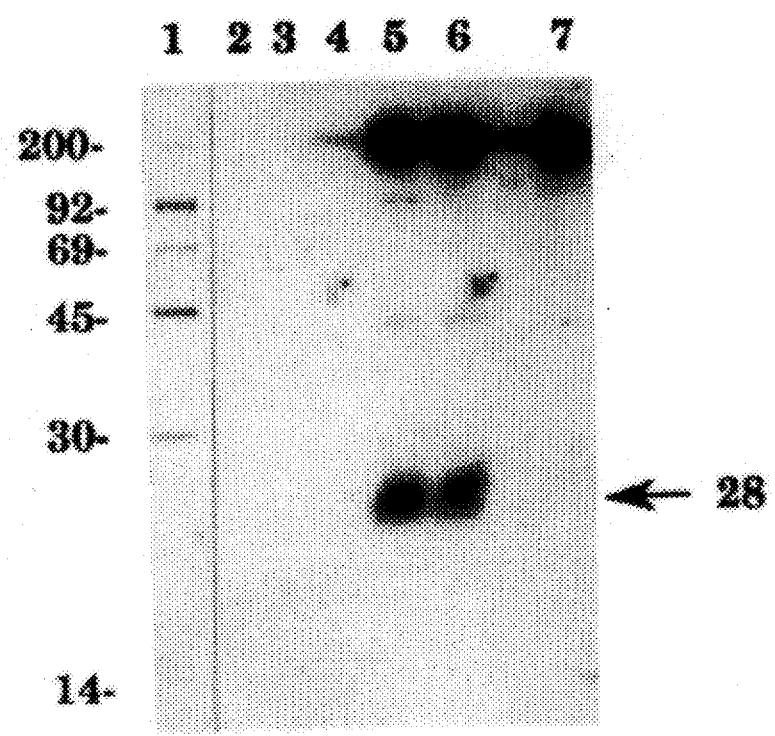
FIG. 13 shows a Western immunoblotting analysis of the various fractions from the immunoaffinity chromatography (shown in FIG. 12). The proteins were electroblotted to nitrocellulose and visualized with monoclonal antibody C7 and $^{125}$I-protein A. Lanes: 1. Molecular weight markers; 2.load; 3. unbound; 4. wash; 5. elution 2; 6. elution 3; 7. monoclonal antibody C7.

The most direct proof of identity of the antiviral factor and sLDLR was obtained by affinity chromatography of the crude antiviral protein on a monoclonal antibody C7 column. This antibody is directed against the ligand binding domain of bovine and human LDLR (Beisiegel, U. et al. (1981) J. Biol. Chem., 256, 11923–11931). Hybridoma C7 (ATCC, CRL 1691) was grown as ascites in mice and immunoglobulin was isolated from the ascitic fluid by ammonium sulfate fractionation. The C7 immunoglobulin (19 mg), was coupled to 1 ml agarose. Partially purified AVH from the 200 mM NaCl fraction of the TSK-DEAE step ("load", 14 ml, 37.8 mg protein, 2800 units) was loaded on the column; the effluent ("effl.") was collected and the column was washed ("wash") with a 70 ml of 0.5M NaCl in phosphate buffered saline (PBS) followed by PBS (30 ml). The column was then eluted with 50 mM $Na_2CO_3$ (pH 11) (el.2 and el.3) with a recovery of 32% (FIG. 12). The amount of protein in the eluted fractions was 15 mg and the degree of purification was 83. SDS-PAGE and silver staining gave many bands. However, on Western blotting (FIG. 13), with mAb C7 (gel run under non-reducing conditions) no receptor was detected in the load, effluent and wash fractions (lanes 2, 3 and 4, respectively). However, the 28K band of the soluble LDL receptor was obtained in el.2 and el.3, (lanes 5 and 6). Also higher molecular weight bands were seen in el.2 and el.3, including weak 40K and 100K bands which probably are larger extracellular fragments of the LDL receptor. The strong band near 200K is probably monoclonal antibody C7 which leaked from the column and reacted with protein A, as it was identical with a C7 sample (lane 7).

Example 5

Induction of Cell Surface LDLR by Interferons

Figure 14:
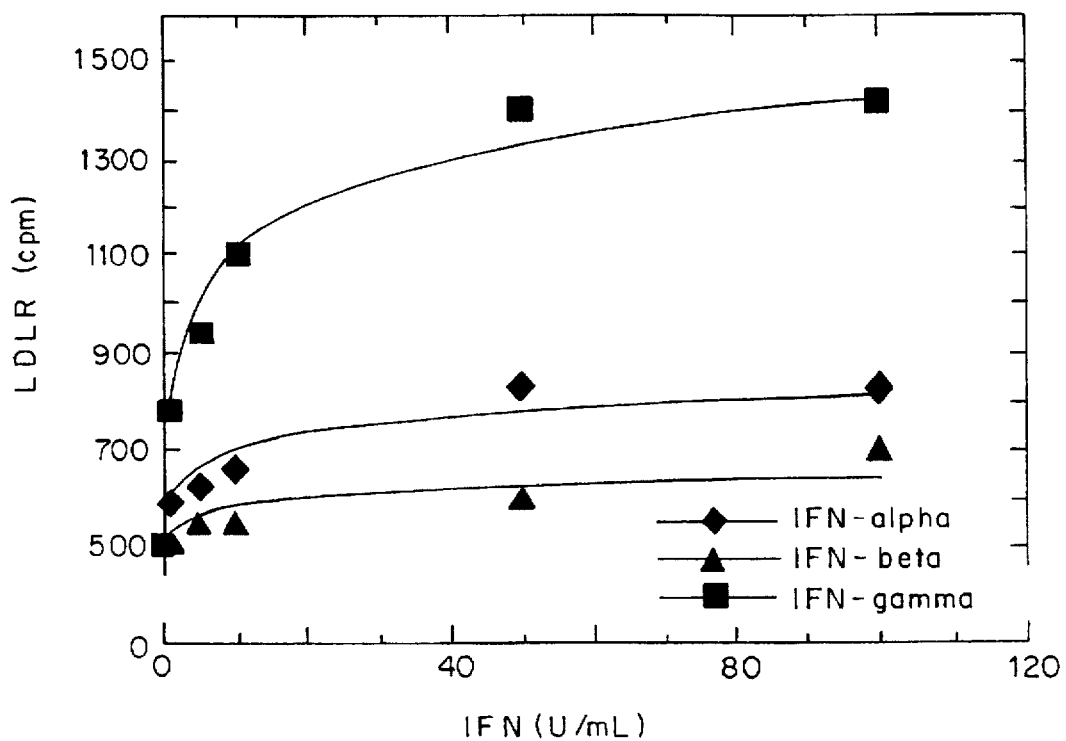
FIG. 14 shows a dose response induction of cell surface LDL receptor in WISH cells by various interferons. Cells were incubated with interferons for 19 hrs in medium containing 2% fetal calf serum and the level of cell surface LDL receptor was then determined by monoclonal antibody C7 and $^{125}$I-protein A.

The ability of interferon to induce soluble LDL receptor suggests that it can also induce cell surface LDL receptor, since both receptor forms share the same gene. To study the possible induction of the full size LDL receptor WISH cells grown to confluence in 1.7 cm wells were incubated with various interferons in medium containing 2% fetal bovine serum. The cells were washed, incubated with monoclonal antibody C7 from 2 hr at 4° C., washed, incubated with $^{125}$I-protein A (about 80,000 dpm) for 2 hr at 4° C., washed, harvested with trypsin and counted. In a time course experiment it was found that maximal induction of LDL receptor with interferon-γ (100 U/ml) occurred between 5 and 23 hr. A dose response study was then performed by incubating WISH cells for 19 hr with different interferons. It was found that interferon γ was the most potent inducer of LDL receptor and maximal induction was seem with 10–50 U/ml. Interferon alpha was a much weaker inducer while interferon beta probably did not induce LRL receptor at all (FIG. 14). The induction of LDL receptor as well as its basal level were abolished in the presence of the protein synthesis inhibitor cycloheximide.

Example 6

Isolation and Purification of Soluble LDL Receptor from Urine

6.1 Preparation of the Urine Concentrate

A pool of 500 liter urine from healthy menopausal women was subjected to microfiltration on a PELLICON membrane with a pore size of 0.45 μm. The filtrate was concentrated by ultrafiltration using a PELLICON membrane with a molecular weight cut off of 10K to a final volume of 700 ml. The concentrate was dialyzed against phosphate buffered saline containing 1 mM benzamidine and 0.1% sodium azide.

6.2 Affinity Chromatography of Soluble LDL Receptor with Monoclonal Antibodies Antibodies against LDL receptor are utilized for the purification of the soluble fragment by affinity chromatography. The monoclonal antibody C7 (ATCC, CRL 1691) was used in this example for affinity chromatography. Ascitic fluid containing the monoclonal antibody secreted by hybridoma C7 was purified by ammonium sulfate precipitation at 50% saturation followed by extensive dialysis against PBS. About 10 mg of immunoglobulin were bound to 1 ml polyacrylhydrazide agarose as specified by Wilchek and Miron, Methods in Enzymology, 34:72076, 1979. Concentrated human urinary proteins (23 g in 730 ml, equivalent to 500 l of crude urine) were loaded on 1.0 ml of the C7 anti-LDL receptor antibody column at 4° C. at a flow rate of 0.25 ml/min. The column was washed with PBS until no protein was detected in the washing. Soluble LDL receptor was eluted by 50 mM $Na_2CO_3$ buffer, pH 11.5, containing 1 mM benzamidine and 0.02% $NaN_3$ (8×1 column volume fractions) and immediately neutralized by 3M acetic acid. Antiviral activity was measured in the eluted fractions and 50,000 units were found in elution fractions no. 2 and 3. The total amount of protein in these fractions was 120 micrograms.

6.3 Reversed Phase HPLC

Figure 16:
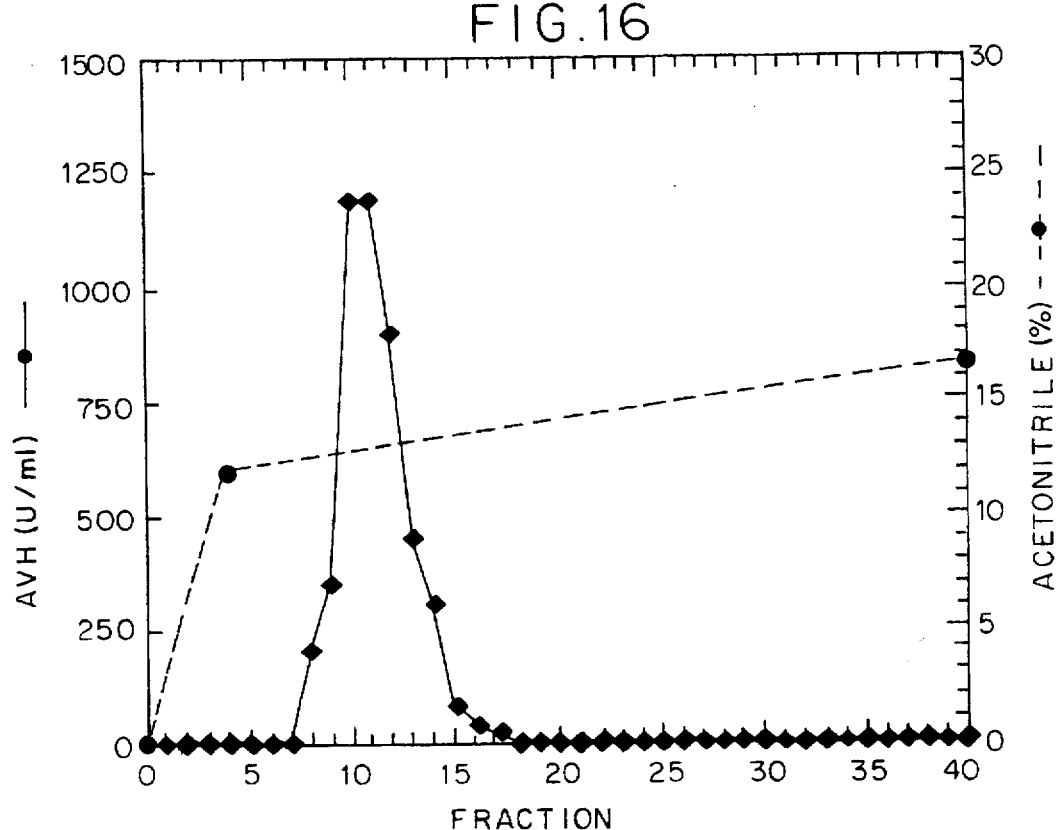
FIG. 16 shows the reversed-phase HPLC of affinity purified urinary soluble LDL receptor. Antiviral activity (AVH) and percentage acetonitrile are indicated.

An aliquot of soluble LDL-R from the affinity chromatography step in 6.2 (32 μg, 8800 units) was loaded on an AQUAPORE RP-300 RP-HPLC column (4.6×30 mm) that was preequilibrated with 20 mM Hepes buffer pH 7.5. The column was washed and eluted at a flow rate of 0.5 ml/min by an acetonitrile gradient in the same buffer. Fractions of 1 ml were collected and tested for antiviral activity. The antiviral activity eluted at 14% acetonitrile (FIG. 16). The column was monitored by flourescamine-based post-column reaction system (Stein S. and Moschera J. (1981) *Methods in Enzymology*, 79:7–16).

Figure 17:
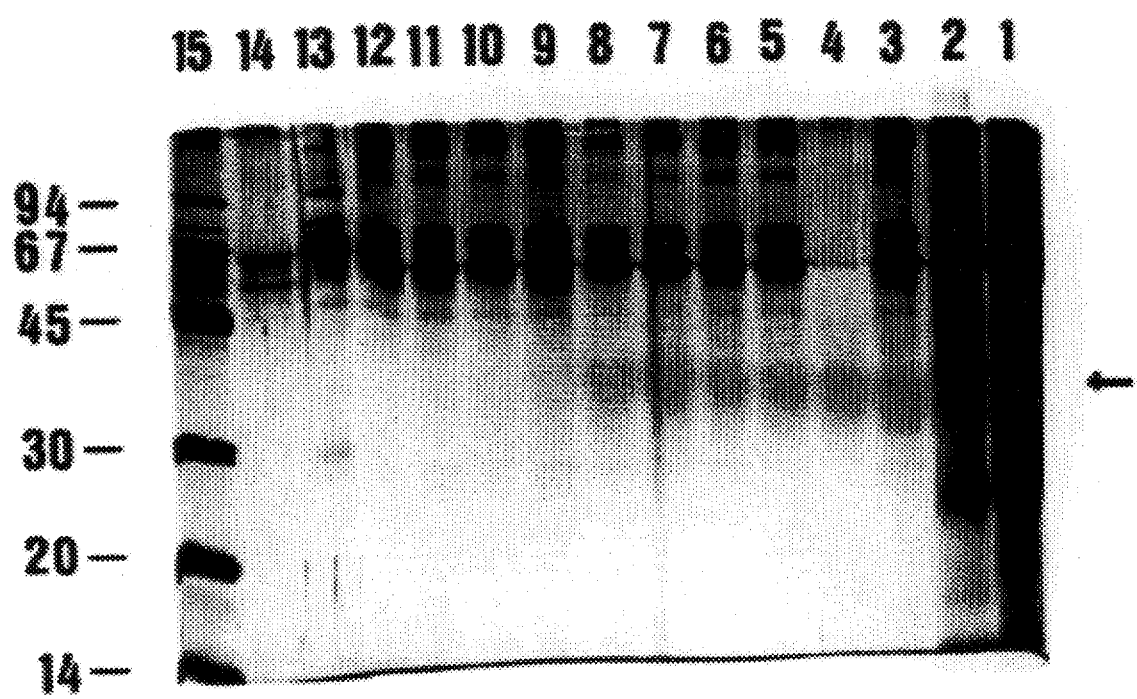
FIG. 17 shows the SDS-PAGE of aliquots of RP-HPLC fractions of FIG. 16.

Aliquots (30 μl) of each fraction were subjected to polyacrylamide (12%) gel electrophoresis in the presence of sodium dodecyl sulfate (SDS-PAGE) (FIG. 17). The protein bands were visualized by silver staining. The lanes (FIG. 17) are: 1. crude urinary proteins; 2. column load (C7 eluate); 3–12. HPLC fractions 9–18 respectively; 13. HPLC fraction 20; 14. control sample buffer; 15. molecular weight markers, indicated on the left side (FIG. 17).

Example 7

Size Exclusion Chromatography of Urinary Soluble LDL, Receptor

Figure 18:
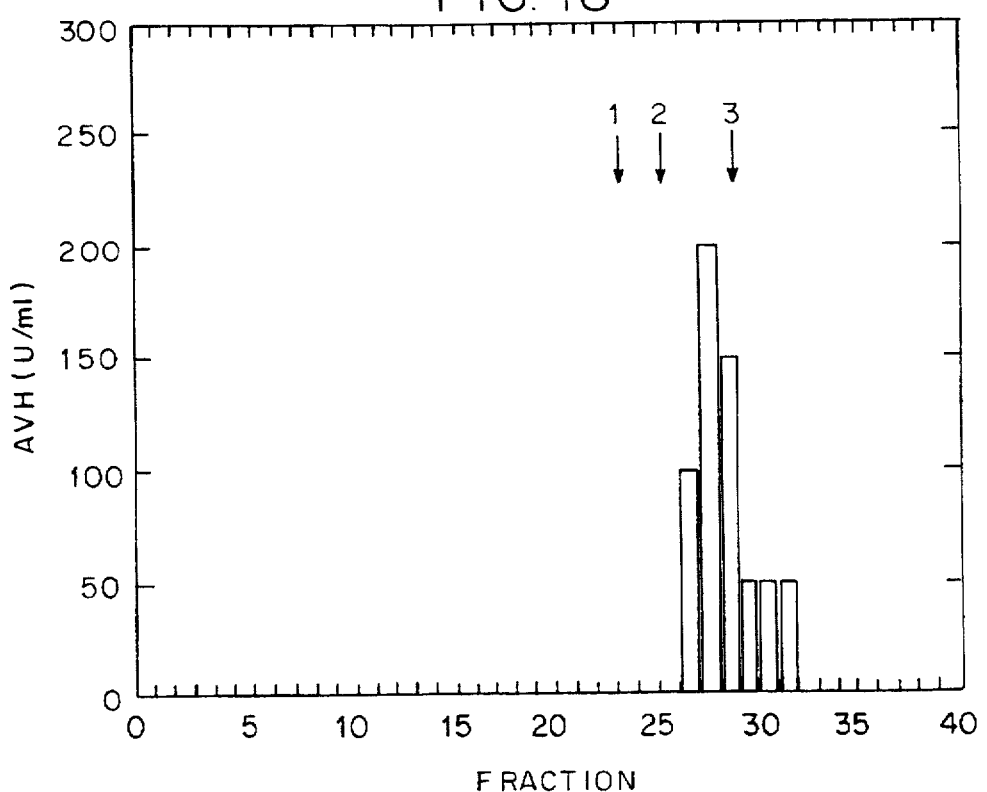
FIG. 18 shows size exclusion chromatography of an aliquot of the affinity-purified urinary soluble LDL receptor. Molecular weight markers elute at the indicated positions: (1) human immunoglobulin (150 kd); (2) bovine serum albumin (67 kd); (3) carbonic anhydrase (30 kd).

Soluble LDL receptor from the affinity chromatography step (1.5 μg, 200 units) was mixed with bovine serum albumin (200 μg), human immunoglobulin (200 μg) in phosphate buffered saline (200 μl total). The mixture was fractionated on a size exclusion column (SUPEROSE 12, 1×30 cm, Pharmacia) in phosphate buffered saline under near physiological conditions. The column was pre-equilibrated and eluted with phosphate buffered saline at a flow rate of 0.5 ml/min. Fractions of 0.5 ml were collected and antiviral activity was measured in each fraction. The column was monitored at 280 nm (FIG. 18). The column was calibrated with human immunoglobulin (150K), bovine serum albumin (67K) and carbonic anhydrase (30K) as molecular weight markers. It was found that the antiviral activity eluted as a peak of apparent molecular weight 30,000, as a range of 26K–34K (FIG. 18).

Example 8

Protein Sequence Analysis and Identification of the Antiviral Factor

Fraction 10 from the RP-HPLC step (1 μg, see 6.3) was absorbed on a PVDF membrane (Prospin, Applied Biosystems, USA) and subjected to microsequence analysis on model 475 protein microsequencer (Applied Biosystems, USA). The resulting sequence of the N-terminal 16 amino acid residues (SEQ ID NO:5) was identified by this system. The amino acids in cycle 3, 10 and 15 were not initially identified, as would be expected for cys residues, but by comparison with the sequence of the human LDL receptor which has cys residues in these positions, these amino acids are cys residues. As can be seen from FIG. 19, the sequence (SEQ ID NO:5) corresponded to a portion of the first fifty residues of the human LDL receptor (SEQ ID NO:2). Thus, the N-terminal sequence of soluble LDL receptor (SEQ ID NO:6) is as shown in SEQ ID NO:5 with cysteine residue at the 3, 10, and 15 positions.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for inhibiting viral infection of a cell comprising treating said cell with a pharmaceutical composition consisting essentially of a pharmaceutically acceptable carrier and an antiviral effective amount of a molecule comprising the soluble antiviral domain of the LDL receptor protein of SEQ ID NO:2, or a functionally equivalent salt, functionally equivalent derivative or functionally equivalent mutein thereof.

2. A method in accordance with claim 1, wherein said molecule comprises the soluble antiviral domain of the LDL receptor protein of SEQ ID NO:2.

3. A method of treating a viral disease in an animal having a viral disease, comprising, administering to said animal a pharmaceutical composition consisting essentially of a pharmaceutically acceptable carrier and an antiviral effective amount of a molecule comprising the soluble antiviral domain of the LDL receptor protein of SEQ ID NO:2, or a functionally equivalent salt, functionally equivalent derivative, or functionally equivalent mutein thereof.

4. A method in accordance with claim 3, wherein said molecule comprises the soluble antiviral domain of the LDL receptor protein of SEQ ID NO:2.

5. A method according to claim 3, wherein said animal is human.

* * * * *

UNITED STATES PATENT AND TRADEMARK OFFICE
CERTIFICATE OF CORRECTION

PATENT NO. : 5,723,438
DATED : March 3, 1998
INVENTOR(S) : Rubinstein et al

It is certified that error appears in the above-identified patent and that said Letters Patent is hereby corrected as shown below:

Column 37, line 17 (claim 1, line 1), change "vital" to --viral--.

Signed and Sealed this

Seventeenth Day of November, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,723,438
DATED : March 3, 1998
INVENTOR(S) : Rubinstein et al.

It is certified that error appears in the above-identified patent and that said Letters Patent is hereby corrected as shown below:

Column 37,
Line 22, change "NO : 2" to -- NO : 4 --.
Line 27, change "NO : 2" to -- NO : 4 --.

Column 38,
Line 19, change "NO : 2" to -- NO : 4 --.
Line 24, change "NO : 2" to -- NO : 4 --.

Signed and Sealed this

Fourth Day of September, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asp Arg Pro Glu Arg Asn Glu Phe Gln Xaa Gln Asp Gly Lys Pro
 1           5                   10                      15
```

( 2 ) INFORMATION FOR SEQ ID NO:2:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Gly Pro Trp Gly Trp Lys Leu Arg Trp Thr Val Ala Leu Leu Leu
 1           5                   10                      15

Ala Ala Ala Gly Thr Ala Val Gly Asp Arg Cys Glu Arg Asn Glu Phe
             20                  25                  30

Gln Cys Gln Asp Gly Lys Cys Ile Ser Tyr Lys Trp Val Cys Asp Gly
         35                  40                  45

Ser Ala
 50
```

( 2 ) INFORMATION FOR SEQ ID NO:3:

( i ) SEQUENCE CHARACTERISTICS:
        ( A ) LENGTH: 5095 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 14..2593

( i x ) FEATURE:
        ( A ) NAME/KEY: mat_peptide
        ( B ) LOCATION: 77..2593

( x i ) SEQUENCE DESCRIPTION: SEQ ID NO:3:

```
AGAGGCTGCG AGC ATG GGG CCC TGG GGC TGG AAA TTG CGC TGG ACC GTC          49
           Met Gly Pro Trp Gly Trp Lys Leu Arg Trp Thr Val
           -21 -20                 -15                 -10

GCC TTG CTC CTC GCC GCG GCG GGG ACT GCA GTG GGC GAC AGA TGT GAA         97
Ala Leu Leu Leu Ala Ala Ala Gly Thr Ala Val Gly Asp Arg Cys Glu
             -5                   1                   5

AGA AAC GAG TTC CAG TGC CAA GAC GGG AAA TGC ATC TCC TAC AAG TGG        145
Arg Asn Glu Phe Gln Cys Gln Asp Gly Lys Cys Ile Ser Tyr Lys Trp
         10                  15                  20
```

| | | | | | | | | | | | | | | | | |
|---|---|---|---|---|---|---|---|---|---|---|---|---|---|---|---|---|
| GTC | TGC | GAT | GGC | AGC | GCT | GAG | TGC | CAG | GAT | GGC | TCT | GAT | GAG | TCC | CAG | 193 |
| Val | Cys | Asp | Gly | Ser | Ala | Glu | Cys | Gln | Asp | Gly | Ser | Asp | Glu | Ser | Gln | |
| | 25 | | | | 30 | | | | | 35 | | | | | | |
| GAG | ACG | TGC | TTG | TCT | GTC | ACC | TGC | AAA | TCC | GGG | GAC | TTC | AGC | TGT | GGG | 241 |
| Glu | Thr | Cys | Leu | Ser | Val | Thr | Cys | Lys | Ser | Gly | Asp | Phe | Ser | Cys | Gly | |
| 40 | | | | | 45 | | | | | 50 | | | | | 55 | |
| GGC | CGT | GTC | AAC | CGC | TGC | ATT | CCT | CAG | TTC | TGG | AGG | TGC | GAT | GGC | CAA | 289 |
| Gly | Arg | Val | Asn | Arg | Cys | Ile | Pro | Gln | Phe | Trp | Arg | Cys | Asp | Gly | Gln | |
| | | | | 60 | | | | | 65 | | | | | 70 | | |
| GTG | GAC | TGC | GAC | AAC | GGC | TCA | GAC | GAG | CAA | GGC | TGT | CCC | CCC | AAG | ACG | 337 |
| Val | Asp | Cys | Asp | Asn | Gly | Ser | Asp | Glu | Gln | Gly | Cys | Pro | Pro | Lys | Thr | |
| | | 75 | | | | | 80 | | | | | 85 | | | | |
| TGC | TCC | CAG | GAC | GAG | TTT | CGC | TGC | CAC | GAT | GGG | AAG | TGC | ATC | TCT | CGG | 385 |
| Cys | Ser | Gln | Asp | Glu | Phe | Arg | Cys | His | Asp | Gly | Lys | Cys | Ile | Ser | Arg | |
| | | 90 | | | | | 95 | | | | | 100 | | | | |
| CAG | TTC | GTC | TGT | GAC | TCA | GAC | CGG | GAC | TGC | TTG | GAC | GGC | TCA | GAC | GAG | 433 |
| Gln | Phe | Val | Cys | Asp | Ser | Asp | Arg | Asp | Cys | Leu | Asp | Gly | Ser | Asp | Glu | |
| | 105 | | | | | 110 | | | | | 115 | | | | | |
| GCC | TCC | TGC | CCG | GTG | CTC | ACC | TGT | GGT | CCC | GCC | AGC | TTC | CAG | TGC | AAC | 481 |
| Ala | Ser | Cys | Pro | Val | Leu | Thr | Cys | Gly | Pro | Ala | Ser | Phe | Gln | Cys | Asn | |
| 120 | | | | | 125 | | | | | 130 | | | | | 135 | |
| AGC | TCC | ACC | TGC | ATC | CCC | CAG | CTG | TGG | GCC | TGC | GAC | AAC | GAC | CCC | GAC | 529 |
| Ser | Ser | Thr | Cys | Ile | Pro | Gln | Leu | Trp | Ala | Cys | Asp | Asn | Asp | Pro | Asp | |
| | | | | 140 | | | | | 145 | | | | | 150 | | |
| TGC | GAA | GAT | GGC | TCG | GAT | GAG | TGG | CCG | CAG | CGC | TGT | AGG | GGT | CTT | TAC | 577 |
| Cys | Glu | Asp | Gly | Ser | Asp | Glu | Trp | Pro | Gln | Arg | Cys | Arg | Gly | Leu | Tyr | |
| | | | 155 | | | | | 160 | | | | | 165 | | | |
| GTG | TTC | CAA | GGG | GAC | AGT | AGC | CCC | TGC | TCG | GCC | TTC | GAG | TTC | CAC | TGC | 625 |
| Val | Phe | Gln | Gly | Asp | Ser | Ser | Pro | Cys | Ser | Ala | Phe | Glu | Phe | His | Cys | |
| | | 170 | | | | | 175 | | | | | 180 | | | | |
| CTA | AGT | GGC | GAG | TGC | ATC | CAC | TCC | AGC | TGG | CGC | TGT | GAT | GGT | GGC | CCC | 673 |
| Leu | Ser | Gly | Glu | Cys | Ile | His | Ser | Ser | Trp | Arg | Cys | Asp | Gly | Gly | Pro | |
| | 185 | | | | | 190 | | | | | 195 | | | | | |
| GAC | TGC | AAG | GAC | AAA | TCT | GAC | GAG | GAA | AAC | TGC | GCT | GTG | GCC | ACC | TGT | 721 |
| Asp | Cys | Lys | Asp | Lys | Ser | Asp | Glu | Glu | Asn | Cys | Ala | Val | Ala | Thr | Cys | |
| 200 | | | | | 205 | | | | | 210 | | | | | 215 | |
| CGC | CCT | GAC | GAA | TTC | CAG | TGC | TCT | GAT | GGA | AAC | TGC | ATC | CAT | GGC | AGC | 769 |
| Arg | Pro | Asp | Glu | Phe | Gln | Cys | Ser | Asp | Gly | Asn | Cys | Ile | His | Gly | Ser | |
| | | | | 220 | | | | | 225 | | | | | 230 | | |
| CGG | CAG | TGT | GAC | CGG | GAA | TAT | GAC | TGC | AAG | GAC | ATG | AGC | GAT | GAA | GTT | 817 |
| Arg | Gln | Cys | Asp | Arg | Glu | Tyr | Asp | Cys | Lys | Asp | Met | Ser | Asp | Glu | Val | |
| | | | 235 | | | | | 240 | | | | | 245 | | | |
| GGC | TGC | GTT | AAT | GTG | ACA | CTC | TGC | GAG | GGA | CCC | AAC | AAG | TTC | AAG | TGT | 865 |
| Gly | Cys | Val | Asn | Val | Thr | Leu | Cys | Glu | Gly | Pro | Asn | Lys | Phe | Lys | Cys | |
| | | 250 | | | | | 255 | | | | | 260 | | | | |
| CAC | AGC | GGC | GAA | TGC | ATC | ACC | CTG | GAC | AAA | GTC | TGC | AAC | ATG | GCT | AGA | 913 |
| His | Ser | Gly | Glu | Cys | Ile | Thr | Leu | Asp | Lys | Val | Cys | Asn | Met | Ala | Arg | |
| | 265 | | | | | 270 | | | | | 275 | | | | | |
| GAC | TGC | CGG | GAC | TGG | TCA | GAT | GAA | CCC | ATC | AAA | GAG | TGC | GGG | ACC | AAC | 961 |
| Asp | Cys | Arg | Asp | Trp | Ser | Asp | Glu | Pro | Ile | Lys | Glu | Cys | Gly | Thr | Asn | |
| 280 | | | | | 285 | | | | | 290 | | | | | 295 | |
| GAA | TGC | TTG | GAC | AAC | AAC | GGC | GGC | TGT | TCC | CAC | GTC | TGC | AAT | GAC | CTT | 1009 |
| Glu | Cys | Leu | Asp | Asn | Asn | Gly | Gly | Cys | Ser | His | Val | Cys | Asn | Asp | Leu | |
| | | | | 300 | | | | | 305 | | | | | 310 | | |
| AAG | ATC | GGC | TAC | GAG | TGC | CTG | TGC | CCC | GAC | GGC | TTC | CAG | CTG | GTG | GCC | 1057 |
| Lys | Ile | Gly | Tyr | Glu | Cys | Leu | Cys | Pro | Asp | Gly | Phe | Gln | Leu | Val | Ala | |
| | | | 315 | | | | | 320 | | | | | 325 | | | |
| CAG | CGA | AGA | TGC | GAA | GAT | ATC | GAT | GAG | TGT | CAG | GAT | CCC | GAC | ACC | TGC | 1105 |
| Gln | Arg | Arg | Cys | Glu | Asp | Ile | Asp | Glu | Cys | Gln | Asp | Pro | Asp | Thr | Cys | |
| | | 330 | | | | | 335 | | | | | 340 | | | | |

```
AGC CAG CTC TGC GTG AAC CTG GAG GGT GGC TAC AAG TGC CAG TGT GAG      1153
Ser Gln Leu Cys Val Asn Leu Glu Gly Gly Tyr Lys Cys Gln Cys Glu
345                     350                 355

GAA GGC TTC CAG CTG GAC CCC CAC ACG AAG GCC TGC AAG GCT GTG GGC      1201
Glu Gly Phe Gln Leu Asp Pro His Thr Lys Ala Cys Lys Ala Val Gly
360                     365                 370                 375

TCC ATC GCC TAC CTC TTC TTC ACC AAC CGG CAC GAG GTC AGG AAG ATG      1249
Ser Ile Ala Tyr Leu Phe Phe Thr Asn Arg His Glu Val Arg Lys Met
                380                 385                 390

ACG CTG GAC CGG AGC GAG TAC ACC AGC CTC ATC CCC AAC CTG AGG AAC      1297
Thr Leu Asp Arg Ser Glu Tyr Thr Ser Leu Ile Pro Asn Leu Arg Asn
            395                 400                 405

GTG GTC GCT CTG GAC ACG GAG GTG GCC AGC AAT AGA ATC TAC TGG TCT      1345
Val Val Ala Leu Asp Thr Glu Val Ala Ser Asn Arg Ile Tyr Trp Ser
        410                 415                 420

GAC CTG TCC CAG AGA ATG ATC TGC AGC ACC CAG CTT GAC AGA GCC CAC      1393
Asp Leu Ser Gln Arg Met Ile Cys Ser Thr Gln Leu Asp Arg Ala His
    425                 430                 435

GGC GTC TCT TCC TAT GAC ACC GTC ATC AGC AGG GAC ATC CAG GCC CCC      1441
Gly Val Ser Ser Tyr Asp Thr Val Ile Ser Arg Asp Ile Gln Ala Pro
440                 445                 450                 455

GAC GGG CTG GCT GTG GAC TGG ATC CAC AGC AAC ATC TAC TGG ACC GAC      1489
Asp Gly Leu Ala Val Asp Trp Ile His Ser Asn Ile Tyr Trp Thr Asp
                460                 465                 470

TCT GTC CTG GGC ACT GTC TCT GTT GCG GAT ACC AAG GGC GTG AAG AGG      1537
Ser Val Leu Gly Thr Val Ser Val Ala Asp Thr Lys Gly Val Lys Arg
            475                 480                 485

AAA ACG TTA TTC AGG GAG AAC GGC TCC AAG CCA AGG GCC ATC GTG GTG      1585
Lys Thr Leu Phe Arg Glu Asn Gly Ser Lys Pro Arg Ala Ile Val Val
        490                 495                 500

GAT CCT GTT CAT GGC TTC ATG TAC TGG ACT GAC TGG GGA ACT CCC GCC      1633
Asp Pro Val His Gly Phe Met Tyr Trp Thr Asp Trp Gly Thr Pro Ala
    505                 510                 515

AAG ATC AAG AAA GGG GGC CTG AAT GGT GTG GAC ATC TAC TCG CTG GTG      1681
Lys Ile Lys Lys Gly Gly Leu Asn Gly Val Asp Ile Tyr Ser Leu Val
520                 525                 530                 535

ACT GAA AAC ATT CAG TGG CCC AAT GGC ATC ACC CTA GAT CTC CTC AGT      1729
Thr Glu Asn Ile Gln Trp Pro Asn Gly Ile Thr Leu Asp Leu Leu Ser
                540                 545                 550

GGC CGC CTC TAC TGG GTT GAC TCC AAA CTT CAC TCC ATC TCA AGC ATC      1777
Gly Arg Leu Tyr Trp Val Asp Ser Lys Leu His Ser Ile Ser Ser Ile
            555                 560                 565

GAT GTC AAT GGG GGC AAC CGG AAG ACC ATC TTG GAG GAT GAA AAG AGG      1825
Asp Val Asn Gly Gly Asn Arg Lys Thr Ile Leu Glu Asp Glu Lys Arg
        570                 575                 580

CTG GCC CAC CCC TTC TCC TTG GCC GTC TTT GAG GAC AAA GTA TTT TGG      1873
Leu Ala His Pro Phe Ser Leu Ala Val Phe Glu Asp Lys Val Phe Trp
    585                 590                 595

ACA GAT ATC ATC AAC GAA GCC ATT TTC AGT GCC AAC CGC CTC ACA GGT      1921
Thr Asp Ile Ile Asn Glu Ala Ile Phe Ser Ala Asn Arg Leu Thr Gly
600                 605                 610                 615

TCC GAT GTC AAC TTG TTG GCT GAA AAC CTA CTG TCC CCA GAG GAT ATG      1969
Ser Asp Val Asn Leu Leu Ala Glu Asn Leu Leu Ser Pro Glu Asp Met
                620                 625                 630

GTC CTC TTC CAC AAC CTC ACC CAG CCA AGA GGA GTG AAC TGG TGT GAG      2017
Val Leu Phe His Asn Leu Thr Gln Pro Arg Gly Val Asn Trp Cys Glu
            635                 640                 645

AGG ACC ACC CTG AGC AAT GGC GGC TGC CAG TAT CTG TGC CTC CCT GCC      2065
Arg Thr Thr Leu Ser Asn Gly Gly Cys Gln Tyr Leu Cys Leu Pro Ala
        650                 655                 660
```

```
CCG CAG ATC AAC CCC CAC TCG CCC AAG TTT ACC TGC GCC TGC CCG GAC      2113
Pro Gln Ile Asn Pro His Ser Pro Lys Phe Thr Cys Ala Cys Pro Asp
        665                 670                 675

GGC ATG CTG CTG GCC AGG GAC ATG AGG AGC TGC CTC ACA GAG GCT GAG      2161
Gly Met Leu Leu Ala Arg Asp Met Arg Ser Cys Leu Thr Glu Ala Glu
680                 685                 690                     695

GCT GCA GTG GCC ACC CAG GAG ACA TCC ACC GTC AGG CTA AAG GTC AGC      2209
Ala Ala Val Ala Thr Gln Glu Thr Ser Thr Val Arg Leu Lys Val Ser
                700                 705                 710

TCC ACA GCC GTA AGG ACA CAG CAC ACA ACC CGG CCT GTT CCC GAC          2257
Ser Thr Ala Val Arg Thr Gln His Thr Thr Thr Arg Pro Val Pro Asp
            715                 720                 725

ACC TCC CGG CTG CCT GGG GCC ACC CCT GGG CTC ACC ACG GTG GAG ATA      2305
Thr Ser Arg Leu Pro Gly Ala Thr Pro Gly Leu Thr Thr Val Glu Ile
        730                 735                 740

GTG ACA ATG TCT CAC CAA GCT CTG GGC GAC GTT GCT GGC AGA GGA AAT      2353
Val Thr Met Ser His Gln Ala Leu Gly Asp Val Ala Gly Arg Gly Asn
Val Thr Met Ser His Gln Ala Leu Gly Asp Val Ala Gly Arg Gly Asn
    745                 750                 755

GAG AAG AAG CCC AGT AGC GTG AGG GCT CTG TCC ATT GTC CTC CCC ATC      2401
Glu Lys Lys Pro Ser Ser Val Arg Ala Leu Ser Ile Val Leu Pro Ile
760                 765                 770                 775

GTG CTC CTC GTC TTC CTT TGC CTG GGG GTC TTC CTT CTA TGG AAG AAC      2449
Val Leu Leu Val Phe Leu Cys Leu Gly Val Phe Leu Leu Trp Lys Asn
                780                 785                 790

TGG CGG CTT AAG AAC ATC AAC AGC ATC AAC TTT GAC AAC CCC GTC TAT      2497
Trp Arg Leu Lys Asn Ile Asn Ser Ile Asn Phe Asp Asn Pro Val Tyr
            795                 800                 805

CAG AAG ACC ACA GAG GAT GAG GTC CAC ATT TGC CAC AAC CAG GAC GGC      2545
Gln Lys Thr Thr Glu Asp Glu Val His Ile Cys His Asn Gln Asp Gly
        810                 815                 820

TAC AGC TAC CCC TCG AGA CAG ATG GTC AGT CTG GAG GAT GAC GTG GCG      2593
Tyr Ser Tyr Pro Ser Arg Gln Met Val Ser Leu Glu Asp Asp Val Ala
825                 830                 835

TGAACATCTG CCTGGAGTCC CGCCCCTGCC CAGAACCCTT CCTGAGACCT CGCCGGCCTT    2653
GTTTTATTCA AAGACAGAGA AGACCAAAGC ATTGCCTGCC AGAGCTTTGT TTTATATATT    2713
TATTCATCTG GGAGGCAGAA CAGGCTTCGG ACAGTGCCCA TGCAATGGCT TGGGTTGGGA    2773
TTTTGGTTTC TTCCTTTCCT GTGAAGGATA AGAGAAACAG GCCCGGGGGG ACCAGGATGA    2833
CACCTCCATT TCTCTCCAGG AAGTTTTGAG TTTCTCTCCA CCGTGACACA ATCCTCAAAC    2893
ATGGAAGATG AAAGGGCAGG GGATGTCAGG CCCAGAGAAG CAAGTGGCTT TCAACACACA    2953
ACAGCAGATG GCACCAACGG GACCCCCTGG CCCTGCCTCA TCCACCAATC TCTAAGCCAA    3013
ACCCCTAAAC TCAGGAGTCA ACGTGTTTAC CTCTTCTATG CAAGCCTTGC TAGACAGCCA    3073
GGTTAGCCTT TGCCCTGTCA CCCCCGAATC ATGACCCACC CAGTGTCTTT CGAGGTGGGT    3133
TTGTACCTTC CTTAAGCCAG GAAAGGGATT CATGGCGTCG GAAATGATCT GGCTGAATCC    3193
GTGGTGGCAC CGAGACCAAA CTCATTCACC AAATGATGCC ACTTCCAGA GGCAGAGCCT     3253
GAGTCACCGG TCACCCTTAA TATTTATTAA GTGCCTGAGA CACCCGGTTA CCTTGGCCGT    3313
GAGGACACGT GGCCTGCACC CAGGTGTGGC TGTCAGGACA CCAGCCTGGT GCCCATCCTC    3373
CCGACCCCTA CCCACTTCCA TTCCCGTGGT CTCCTTGCAC TTTCTCAGTT CAGAGTTGTA    3433
CACTGTGTAC ATTTGGCATT TGTGTTATTA TTTTGCACTG TTTTCTGTCG TGTGTGTTGG    3493
GATGGGATCC CAGGCCAGGG AAAGCCCGTG TCAATGAATG CCGGGGACAG AGAGGGGCAG    3553
GTTGACCGGG ACTTCAAAGC CGTGATCGTG AATATCGAGA ACTGCCATTG TCGTCTTTAT    3613
GTCCGCCCAC CTAGTGCTTC CACTTCTATG CAAATGCCTC CAAGCCATTC ACTTCCCCAA    3673
```

```
TCTTGTCGTT GATGGGTATG TGTTTAAAAC ATGCACGGTG AGGCCGGGCG CAGTGGCCTC    3733
ACGCCTGTAA TCCCAGCACT TTGGGAGGCC GAGGCGGGTG GATCATGAGG TCAGGAGATC    3793
GAGACCATCC TGGCTAACAA GGTGAAACCC CGTCTCTACT AAAAATACAA AAAATTAGCC    3853
GGGCGCGGTG GTGGGCACCT GTAGTCCCAG CTACTCGGGA GGCTGAGGCA GGAGAATGGT    3913
GTGAACCCGG GAAGCGGAGC TTGCAGTGAG CCGAGATTGC GCCACTGCAG TCCGCAGTCT    3973
GGCCTGGGCG ACAGAGCGAG ACTCCGTCTC AAAAAAAACA AACAAAAAA AAACCATGCA     4033
TGGTGCATCA GCAGCCCATG GCCTCTGGCC AGGCATGGCG AGGCTGAGGT GGGAGGATGG    4093
TTTGAGCTCA GGCATTTGAG GCTGTCGTGA GCTATGATTA TGCCACTGCT TTCCAGCCTG    4153
GGCAACATAG TAAGACCCCA TCTCTTAAAA AATGAATTTG GCCAGACACA GGTGCCTCAC    4213
GCCTGTAATC CCAGCACTTT GGGAGGCTGA GCTGGATCAC TTGAGTTCAG GAGTTGGAGA    4273
CCAGGCCTGA GCAACAAAGC GAGATCCCAT CTCTACAAAA ACCAAAAAGT TAAAAATCAG    4333
CTGGGTATGG TGGCACGTGC CTGTGATCCC AGCTACTTGG GAGGCTGAGG CAGGAGGATC    4393
GCCTGAGCCC AGGAGGTGGA GGTTGCAGTG AGCCATGATC GAGCCACTGC ACTCCAGCCT    4453
GGGCAACAGA TGAAGACCCT ATTTCAGAAA TACAACTATA AAAAAAATAA ATAAATCCTC    4513
CAGTCTGGAT CGTTTGACGG GACTTCAGGT TCTTTCTGAA ATCGCCGTGT TACTGTTGCA    4573
CTGATGTCCG GAGAGACAGT GACAGCCTCC GTCAGACTCC CGCGTGAAGA TGTCACAAGG    4633
GATTGGCAAT TGTCCCCAGG GACAAAACAC TGTGTCCCCC CCAGTGCAGG GAACCGTGAT    4693
AAGCCTTTCT GGTTCGGAG CACGTAAATG CGTCCTGTA CAGATAGTGG GGATTTTTG      4753
TTATGTTTGC ACTTTGTATA TTGGTTGAAA CTGTTATCAC TTATATATAT ATATACACAC    4813
ATATATATAA AATCTATTTA TTTTTGCAAA CCCTGGTTGC TGTATTGTT CAGTGACTAT     4873
TCTCGGGGCC CTGTGTAGGG GGTTATTGCC TCTGAAATGC CTCTTCTTTA TGTACAAAGA    4933
TTATTTGCAC GAACTGGACT GTGTGCAACG CTTTTGGGA GAATGATGTC CCCGTTGTAT     4993
GTATGAGTGG CTTCTGGGAG ATGGGTGTCA CTTTTAAAC CACTGTATAG AAGGTTTTG      5053
TAGCCTGAAT GTCTTACTGT GATCAATTAA ATTTCTTAAA TG                       5095
```

( 2 ) INFORMATION FOR SEQ ID NO:4:

( i ) SEQUENCE CHARACTERISTICS:
        ( A ) LENGTH: 860 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Gly  Pro  Trp  Gly  Trp  Lys  Leu  Arg  Trp  Thr  Val  Ala  Leu  Leu  Leu
-21  -20            -15                      -10

Ala  Ala  Ala  Gly  Thr  Ala  Val  Gly  Asp  Arg  Cys  Glu  Arg  Asn  Glu  Phe
 -5             1                      5                       10

Gln  Cys  Gln  Asp  Gly  Lys  Cys  Ile  Ser  Tyr  Lys  Trp  Val  Cys  Asp  Gly
           15                      20                      25

Ser  Ala  Glu  Cys  Gln  Asp  Gly  Ser  Asp  Glu  Ser  Gln  Glu  Thr  Cys  Leu
           30                      35                      40

Ser  Val  Thr  Cys  Lys  Ser  Gly  Asp  Phe  Ser  Cys  Gly  Gly  Arg  Val  Asn
           45                      50                      55

Arg  Cys  Ile  Pro  Gln  Phe  Trp  Arg  Cys  Asp  Gly  Gln  Val  Asp  Cys  Asp
 60                      65                      70                      75

Asn  Gly  Ser  Asp  Glu  Gln  Gly  Cys  Pro  Pro  Lys  Thr  Cys  Ser  Gln  Asp
```

-continued

|     |     |     |     | 80  |     |     |     |     | 85  |     |     |     |     | 90  |     |
| --- | --- | --- | --- | --- | --- | --- | --- | --- | --- | --- | --- | --- | --- | --- | --- |
| Glu | Phe | Arg | Cys | His | Asp | Gly | Lys | Cys | Ile | Ser | Arg | Gln | Phe | Val | Cys |
|     |     |     | 95  |     |     |     |     | 100 |     |     |     | 105 |     |     |     |
| Asp | Ser | Asp | Arg | Asp | Cys | Leu | Asp | Gly | Ser | Asp | Glu | Ala | Ser | Cys | Pro |
|     |     | 110 |     |     |     | 115 |     |     |     | 120 |     |     |     |     |     |
| Val | Leu | Thr | Cys | Gly | Pro | Ala | Ser | Phe | Gln | Cys | Asn | Ser | Ser | Thr | Cys |
|     | 125 |     |     |     |     | 130 |     |     |     |     | 135 |     |     |     |     |
| Ile | Pro | Gln | Leu | Trp | Ala | Cys | Asp | Asn | Asp | Pro | Asp | Cys | Glu | Asp | Gly |
| 140 |     |     |     |     | 145 |     |     |     |     | 150 |     |     |     |     | 155 |
| Ser | Asp | Glu | Trp | Pro | Gln | Arg | Cys | Arg | Gly | Leu | Tyr | Val | Phe | Gln | Gly |
|     |     |     |     | 160 |     |     |     |     | 165 |     |     |     |     | 170 |     |
| Asp | Ser | Ser | Pro | Cys | Ser | Ala | Phe | Glu | Phe | His | Cys | Leu | Ser | Gly | Glu |
|     |     |     | 175 |     |     |     |     | 180 |     |     |     |     | 185 |     |     |
| Cys | Ile | His | Ser | Ser | Trp | Arg | Cys | Asp | Gly | Gly | Pro | Asp | Cys | Lys | Asp |
|     |     | 190 |     |     |     |     | 195 |     |     |     |     | 200 |     |     |     |
| Lys | Ser | Asp | Glu | Glu | Asn | Cys | Ala | Val | Ala | Thr | Cys | Arg | Pro | Asp | Glu |
|     | 205 |     |     |     |     | 210 |     |     |     |     | 215 |     |     |     |     |
| Phe | Gln | Cys | Ser | Asp | Gly | Asn | Cys | Ile | His | Gly | Ser | Arg | Gln | Cys | Asp |
| 220 |     |     |     |     | 225 |     |     |     |     | 230 |     |     |     |     | 235 |
| Arg | Glu | Tyr | Asp | Cys | Lys | Asp | Met | Ser | Asp | Glu | Val | Gly | Cys | Val | Asn |
|     |     |     |     | 240 |     |     |     |     | 245 |     |     |     |     | 250 |     |
| Val | Thr | Leu | Cys | Glu | Gly | Pro | Asn | Lys | Phe | Lys | Cys | His | Ser | Gly | Glu |
|     |     |     | 255 |     |     |     |     | 260 |     |     |     |     | 265 |     |     |
| Cys | Ile | Thr | Leu | Asp | Lys | Val | Cys | Asn | Met | Ala | Arg | Asp | Cys | Arg | Asp |
|     |     | 270 |     |     |     |     | 275 |     |     |     |     | 280 |     |     |     |
| Trp | Ser | Asp | Glu | Pro | Ile | Lys | Glu | Cys | Gly | Thr | Asn | Glu | Cys | Leu | Asp |
|     | 285 |     |     |     |     | 290 |     |     |     |     | 295 |     |     |     |     |
| Asn | Asn | Gly | Gly | Cys | Ser | His | Val | Cys | Asn | Asp | Leu | Lys | Ile | Gly | Tyr |
| 300 |     |     |     |     | 305 |     |     |     |     | 310 |     |     |     |     | 315 |
| Glu | Cys | Leu | Cys | Pro | Asp | Gly | Phe | Gln | Leu | Val | Ala | Gln | Arg | Arg | Cys |
|     |     |     |     | 320 |     |     |     |     | 325 |     |     |     |     | 330 |     |
| Glu | Asp | Ile | Asp | Glu | Cys | Gln | Asp | Pro | Asp | Thr | Cys | Ser | Gln | Leu | Cys |
|     |     |     | 335 |     |     |     |     | 340 |     |     |     |     | 345 |     |     |
| Val | Asn | Leu | Glu | Gly | Gly | Tyr | Lys | Cys | Gln | Cys | Glu | Glu | Gly | Phe | Gln |
|     |     | 350 |     |     |     |     | 355 |     |     |     |     | 360 |     |     |     |
| Leu | Asp | Pro | His | Thr | Lys | Ala | Cys | Lys | Ala | Val | Gly | Ser | Ile | Ala | Tyr |
|     | 365 |     |     |     |     | 370 |     |     |     |     | 375 |     |     |     |     |
| Leu | Phe | Phe | Thr | Asn | Arg | His | Glu | Val | Arg | Lys | Met | Thr | Leu | Asp | Arg |
| 380 |     |     |     |     | 385 |     |     |     |     | 390 |     |     |     |     | 395 |
| Ser | Glu | Tyr | Thr | Ser | Leu | Ile | Pro | Asn | Leu | Arg | Asn | Val | Val | Ala | Leu |
|     |     |     |     | 400 |     |     |     |     | 405 |     |     |     |     | 410 |     |
| Asp | Thr | Glu | Val | Ala | Ser | Asn | Arg | Ile | Tyr | Trp | Ser | Asp | Leu | Ser | Gln |
|     |     |     | 415 |     |     |     |     | 420 |     |     |     |     | 425 |     |     |
| Arg | Met | Ile | Cys | Ser | Thr | Gln | Leu | Asp | Arg | Ala | His | Gly | Val | Ser | Ser |
|     |     | 430 |     |     |     |     | 435 |     |     |     |     | 440 |     |     |     |
| Tyr | Asp | Thr | Val | Ile | Ser | Arg | Asp | Ile | Gln | Ala | Pro | Asp | Gly | Leu | Ala |
|     | 445 |     |     |     |     | 450 |     |     |     |     | 455 |     |     |     |     |
| Val | Asp | Trp | Ile | His | Ser | Asn | Ile | Tyr | Trp | Thr | Asp | Ser | Val | Leu | Gly |
| 460 |     |     |     |     | 465 |     |     |     |     | 470 |     |     |     |     | 475 |
| Thr | Val | Ser | Val | Ala | Asp | Thr | Lys | Gly | Val | Lys | Arg | Lys | Thr | Leu | Phe |
|     |     |     |     | 480 |     |     |     |     | 485 |     |     |     |     | 490 |     |
| Arg | Glu | Asn | Gly | Ser | Lys | Pro | Arg | Ala | Ile | Val | Val | Asp | Pro | Val | His |
|     |     |     | 495 |     |     |     |     | 500 |     |     |     |     | 505 |     |     |

-continued

| | | | | | | | | | | | | | | |
|---|---|---|---|---|---|---|---|---|---|---|---|---|---|---|
| Gly | Phe | Met 510 | Tyr | Trp | Thr | Asp | Trp 515 | Gly | Thr | Pro | Ala | Lys 520 | Ile | Lys | Lys |
| Gly | Gly 525 | Leu | Asn | Gly | Val | Asp 530 | Ile | Tyr | Ser | Leu | Val 535 | Thr | Glu | Asn | Ile |
| Gln 540 | Trp | Pro | Asn | Gly | Ile 545 | Thr | Leu | Asp | Leu | Leu 550 | Ser | Gly | Arg | Leu | Tyr 555 |
| Trp | Val | Asp | Ser | Lys 560 | Leu | His | Ser | Ile | Ser 565 | Ser | Ile | Asp | Val | Asn 570 | Gly |
| Gly | Asn | Arg | Lys 575 | Thr | Ile | Leu | Glu | Asp 580 | Glu | Lys | Arg | Leu | Ala 585 | His | Pro |
| Phe | Ser | Leu 590 | Ala | Val | Phe | Glu | Asp 595 | Lys | Val | Phe | Trp | Thr 600 | Asp | Ile | Ile |
| Asn | Glu 605 | Ala | Ile | Phe | Ser | Ala 610 | Asn | Arg | Leu | Thr | Gly 615 | Ser | Asp | Val | Asn |
| Leu 620 | Leu | Ala | Glu | Asn | Leu 625 | Leu | Ser | Pro | Glu | Asp 630 | Met | Val | Leu | Phe | His 635 |
| Asn | Leu | Thr | Gln | Pro 640 | Arg | Gly | Val | Asn | Trp 645 | Cys | Glu | Arg | Thr | Thr 650 | Leu |
| Ser | Asn | Gly | Gly 655 | Cys | Gln | Tyr | Leu | Cys 660 | Leu | Pro | Ala | Pro | Gln 665 | Ile | Asn |
| Pro | His | Ser 670 | Pro | Lys | Phe | Thr | Cys 675 | Ala | Cys | Pro | Asp | Gly 680 | Met | Leu | Leu |
| Ala | Arg 685 | Asp | Met | Arg | Ser | Cys 690 | Leu | Thr | Glu | Ala | Glu 695 | Ala | Ala | Val | Ala |
| Thr 700 | Gln | Glu | Thr | Ser | Thr 705 | Val | Arg | Leu | Lys | Val 710 | Ser | Ser | Thr | Ala | Val 715 |
| Arg | Thr | Gln | His | Thr 720 | Thr | Thr | Arg | Pro | Val 725 | Pro | Asp | Thr | Ser | Arg 730 | Leu |
| Pro | Gly | Ala | Thr 735 | Pro | Gly | Leu | Thr | Thr 740 | Val | Glu | Ile | Val | Thr 745 | Met | Ser |
| His | Gln | Ala 750 | Leu | Gly | Asp | Val | Ala 755 | Gly | Arg | Gly | Asn | Glu 760 | Lys | Lys | Pro |
| Ser | Ser 765 | Val | Arg | Ala | Leu | Ser 770 | Ile | Val | Leu | Pro | Ile 775 | Val | Leu | Leu | Val |
| Phe 780 | Leu | Cys | Leu | Gly | Val 785 | Phe | Leu | Leu | Trp | Lys 790 | Asn | Trp | Arg | Leu | Lys 795 |
| Asn | Ile | Asn | Ser | Ile 800 | Asn | Phe | Asp | Asn | Pro 805 | Val | Tyr | Gln | Lys | Thr 810 | Thr |
| Glu | Asp | Glu | Val 815 | His | Ile | Cys | His | Asn 820 | Gln | Asp | Gly | Tyr | Ser 825 | Tyr | Pro |
| Ser | Arg | Gln 830 | Met | Val | Ser | Leu | Glu 835 | Asp | Asp | Val | Ala | | | | |

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| | | | | | | | | | | | | | | |
|---|---|---|---|---|---|---|---|---|---|---|---|---|---|---|
| Asp 1 | Arg | Xaa | Glu | Arg 5 | Asn | Glu | Phe | Gln | Xaa 10 | Gln | Asp | Gly | Lys | Xaa 15 | Ile |

(2) INFORMATION FOR SEQ ID NO:6:

(i) SEQUENCE CHARACTERISTICS:
  (A) LENGTH: 16 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:6:

```
Asp Arg Cys Glu Arg Asn Glu Phe Gln Cys Gln Asp Gly Lys Cys Ile
 1           5                  10                  15
```